United States Patent
Bausch

(10) Patent No.: US 11,285,155 B2
(45) Date of Patent: Mar. 29, 2022

(54) PHARMACEUTICAL COMBINATIONS FOR TREATING CANCER

(71) Applicant: SUPPORT-VENTURE GMBH, Basel (CH)

(72) Inventor: Alexander Bausch, Riehen (CH)

(73) Assignee: SUPPORT-VENTURE GMBH, Basel (CH)

(*) Notice: Subject to any disclaimer, the term of this patent is extended or adjusted under 35 U.S.C. 154(b) by 0 days.

(21) Appl. No.: 16/307,860

(22) PCT Filed: Jun. 6, 2017

(86) PCT No.: PCT/EP2017/063714
§ 371 (c)(1),
(2) Date: Dec. 6, 2018

(87) PCT Pub. No.: WO2017/211830
PCT Pub. Date: Dec. 14, 2017

(65) Prior Publication Data
US 2019/0160072 A1    May 30, 2019

(30) Foreign Application Priority Data
Jun. 8, 2016 (EP) .................... 16173443

(51) Int. Cl.
*A61K 31/519* (2006.01)
*A61P 35/04* (2006.01)
*A61K 31/27* (2006.01)
*A61K 45/06* (2006.01)
*A61K 31/4439* (2006.01)
*A61K 31/427* (2006.01)

(52) U.S. Cl.
CPC .......... *A61K 31/519* (2013.01); *A61K 31/427* (2013.01); *A61K 31/4439* (2013.01); *A61K 45/06* (2013.01); *A61P 35/04* (2018.01)

(58) Field of Classification Search
CPC .. A61K 31/519; A61K 31/4439; A61K 45/06; A61K 31/427; A61K 2300/00; A61P 35/04; A61P 35/00
See application file for complete search history.

(56) References Cited

FOREIGN PATENT DOCUMENTS

| WO | 02/064594 A2 | 8/2002 | |
| WO | WO-03059294 A2 * | 7/2003 | ........... A61K 31/192 |
| WO | 2006/127678 A2 | 11/2006 | |
| WO | 2007/146712 A2 | 12/2007 | |
| WO | 2010/071583 A1 | 6/2010 | |
| WO | WO-2011100769 A2 * | 8/2011 | ............. A61K 47/55 |

OTHER PUBLICATIONS

International Search Report issued in International Application No. PCT/EP2017/063714, dated Jun. 8, 2016.
Elrod et al., "PPARγ and Apoptosis in Cancer," PPAR Research (2008), Article ID 704165, pp. 1-12.
Jung et al., "Role of mitogen-activated protein kinase (MAPK) in troglitazone-induced osteoblastic cell death," Toxicology 234:73-82 (2007).
Huoyan et al., "PPARγ agonist pioglitazone inhibits microglia inflammation by blocking p38 mitogen-activated protein kinase signaling pathways," Inflamm. Res. 59:921-929 (2010).
Barger et al.,"p38 Mitogen-activated Protein Kinase Activates Peroxisome Proliferator-activated Receptor α," J. Biol. Chem. 276(48) 48:44495-44501 (2001).

* cited by examiner

*Primary Examiner* — Sarah Pihonak
*Assistant Examiner* — Jason Deck
(74) *Attorney, Agent, or Firm* — Medier Ferro Woodhouse & Mills PLLC

(57) ABSTRACT

The present invention relates to pharmaceutical combinations comprising a PPAR agonist and a P38 inhibitor for use in a method for the prevention, delay of progression or treatment of cancer.

4 Claims, 4 Drawing Sheets

PHARMACEUTICAL COMBINATIONS FOR TREATING CANCER

FIELD OF THE INVENTION

The present invention relates to pharmaceutical combinations comprising a PPAR agonist and a P38 inhibitor for use in a method for the prevention, delay of progression or treatment of cancer in a subject.

BACKGROUND OF THE INVENTION

Despite the ever increasing number of cancer therapies in general, and combination cancer therapies in particular, cancer is still the third most common cause of death worldwide after cardiovascular diseases and infectious/parasitic diseases; in absolute numbers, this corresponds to 7.6 million deaths (ca. 13% of all deaths) in any given year. The WHO estimates deaths due to cancer to increase to 13.1 million by 2030, while the American Cancer Society expects over 1,685,210 new cancer cases diagnosed and 595,690 cancer deaths in the US in 2016. A 2012 survey by McMillan Cancer Support in the UK has revealed that the median survival time of cancer patients overall has increased from 1 year to 6 years since the 1970's. However, for many cancers including esophageal-, stomach-, lung-, brain- and pancreatic cancer, median survival has barely improved, remaining less than one year. These statistics illustrate the fact that cancer remains a critical health condition and that there is an urgent need for new anticancer drugs.

The rationale for combination chemotherapy in cancer is to use drugs that work by different mechanisms, thereby decreasing the likelihood that resistant cancer cells will develop. On the other hand, administration of two or more drugs to treat a given condition, such as cancer, generally raises a number of potential problems due to complex in vivo interactions between drugs. The effects of any single drug are related to its absorption, distribution, and elimination. When two drugs are introduced into the body, each drug can affect the absorption, distribution, and elimination of the other and hence, alter the effects of the other. For instance, one drug may inhibit, activate or induce the production of enzymes involved in a metabolic route of elimination of the other drug. Thus, when two drugs are administered to treat the same condition, it is unpredictable whether each will complement, have no effect on, or interfere with, the therapeutic activity of the other in a subject. Not only may the interaction between two drugs affect the intended therapeutic activity of each drug, but the interaction may increase the levels of toxic metabolites. The interaction may also heighten or lessen the side effects of each drug. Hence, upon administration of two drugs to treat a disease, it is unpredictable what change, either deterioration or improvement, will occur in the side effect profile of each drug. Additionally, it is difficult to accurately predict when the effects of the interaction between the two drugs will become manifest. For example, metabolic interactions between drugs may become apparent upon the initial administration of the second drug, after the two have reached a steady-state concentration or upon discontinuation of one of the drugs. Therefore, the effects of a combination therapy of two or more drugs cannot be easily predicted.

SUMMARY OF THE INVENTION

It has now unexpectedly been found that a combination comprising a PPAR agonist, such as pioglitazone and a P38 inhibitor, such as pamapimod is useful for the prevention, delay of progression or treatment of cancer, in particular lung cancer, ovarian cancer, prostate cancer, breast cancer, bladder cancer, liver cancer, cancer of the gastrointestinal tract, hematological cancer or kidney cancer. In a standard model established in cancer research, it was unexpectedly found that treatment with said combination provides an increased anti-tumor effect above the effect of either agent alone.

Taking these unexpected findings into account, the inventors herewith provide the present invention in its following aspects.

In a first aspect the present invention provides a pharmaceutical combination comprising:
(a) a PPAR agonist;
(b) a compound of the formula I or II

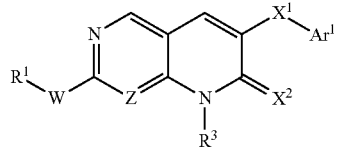

Formula I

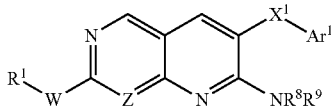

Formula II or pharmaceutically acceptable salts thereof, wherein

Z is N or CH;

W is $NR^2$;

$X^1$ is O, $NR^4$ (where $R^4$ is hydrogen or alkyl), S, or $CR^5R^6$ (where $R^5$ and $R^6$ are independently hydrogen or alkyl) or C=O;

$X^2$ is O or $NR^7$;

$Ar^1$ is aryl or heteroaryl;

$R^2$ is hydrogen, alkyl, acyl, alkoxycarbonyl, aryloxycarbonyl, heteroalkylcarbonyl, heteroalkyloxycarbonyl or —$R^{21}$-$R^{22}$ where $R^{21}$ is alkylene or —C(=O)— and $R^{22}$ is alkyl or alkoxy;

$R^1$ is hydrogen, alkyl, haloalkyl, aryl, aralkyl, heteroaryl, heteroalkyl, heteroaralkyl, cycloalkyl, cycloalkylalkyl, heteroalkylsubstituted cycloalkyl, heterosubstituted cycloalkyl, cyanoalkyl, heterocyclyl, heterocyclylalkyl, $R^{12}$—$SO_2$-heterocycloamino (where $R^{12}$ is haloalkyl, aryl, aralkyl, heteroaryl or heteroaralkyl), —$Y^1$—C(O)—$Y^2$—$R^{11}$ (where $Y^1$ and $Y^2$ are independently either absent or an alkylene group and $R^{11}$ is hydrogen, alkyl, haloalkyl, hydroxy, alkoxy, amino, monoalkylamino or dialkylamino), (heterocyclyl)(cycloalkyl)alkyl or (heterocyclyl)(heteroaryl)alkyl;

$R^3$ is hydrogen, alkyl, cycloalkyl, cycloalkylalkyl, aryl, aralkyl, haloalkyl, heteroalkyl, cyanoalkyl, alkylene-C(O)—$R^{31}$ (where $R^{31}$ is hydrogen, alkyl, hydroxy, alkoxy, amino, monoalkylamino or dialkylamino), amino, monoalkylamino, dialkylamino or $NR^{32}$—$Y^3$—$R^{33}$ (where $Y^3$ is —C(O), —C(O)O—, —C(O)$NR^{34}$, $S(O)_2$ or $S(O)_2NR^{35}$; $R^{32}$, $R^{34}$ and $R^{35}$ are independently hydrogen or alkyl; and $R^{33}$ is hydrogen, alkyl, cycloalkyl, cycloalkylalkyl, heteroalkyl or optionally substituted phenyl) or acyl;

$R^7$ is hydrogen or alkyl; and $R^8$ and $R^9$ are independently hydrogen, alkyl, aryl, aralkyl, cycloalkyl, cycloalkylalkyl, heteroalkyl, alkylsulfonyl, arylsulfonyl, —C(O)—$R^{81}$ (where $R^{81}$ is alkyl, aryl, aralkyl, cycloalkyl, cycloalkylalkyl, heteroalkyl, alkoxy, aryloxy, amino, mono- or dialkylamino, arylamino or aryl(alkyl)amino) or $R^8$ and $R^9$ together form =$CR^{82}R^{83}$ (where $R^{82}$ and $R^{83}$ are independently hydrogen, alkyl, cycloalkyl, cycloalkylalkyl or optionally substituted phenyl);

and optionally (c) one or more pharmaceutically acceptable diluents, excipients or carriers.

In a second aspect the present invention provides a pharmaceutical combination as described herein, for use as a medicament.

In a third aspect the present invention provides a pharmaceutical combination as described herein, for use in a method for the prevention, delay of progression or treatment of cancer in a subject.

In a fourth aspect the present invention provides a pharmaceutical combination comprising:
(a) a PPAR agonist;
(b) a p38 kinase inhibitor; and optionally
(c) one or more pharmaceutically acceptable diluents, excipients or carriers
for use in a method for the prevention, delay of progression or treatment of lung cancer or ovarian cancer in a subject.

DETAILED DESCRIPTION OF THE INVENTION

Figure 1:
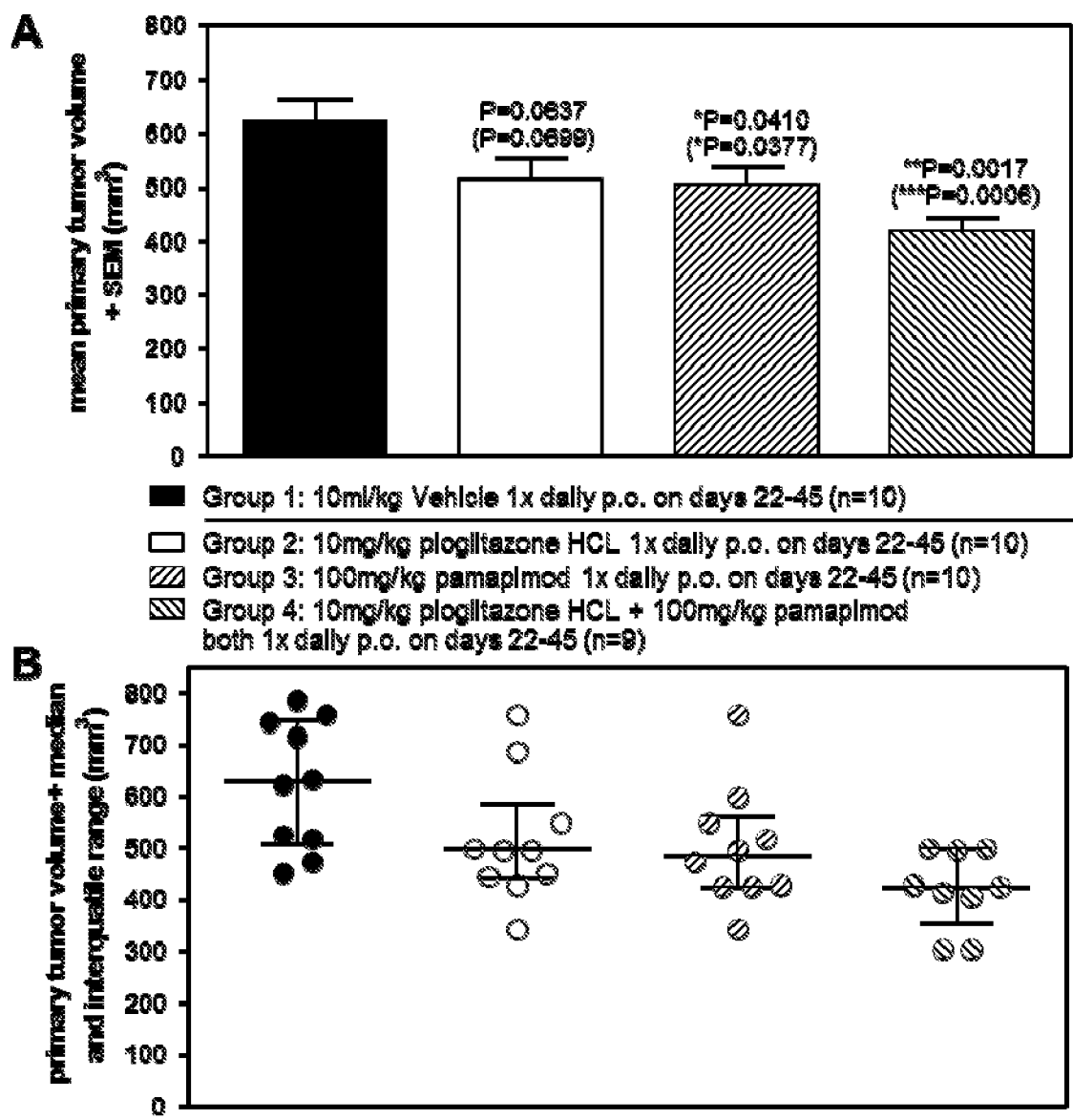
FIG. 1: Primary tumor volumes measures after necropsy performed on day 46 of the study in a subcutaneous xenograft A549 lung carcinoma model described in Example 1. Pioglitazone HCL and pamapimod were administered both alone (Groups 2 and 3, respectively) and in combination (Group 4). Data are displayed versus the Vehicle Control (Group 1). Data are depicted both as means+SEM (A) and as individual data points together with their corresponding median values and interquartile ranges (B). P-values were calculated compared to the Vehicle Control (Group 1) by two methods: using the Mann Whitney test and the unpaired t-test (in parentheses).

As outlined above, the present invention provides pharmaceutical combinations comprising a PPAR agonist, such as pioglitazone and a P38 inhibitor, such as pamapimod, which are useful for the prevention, delay of progression, or treatment of cancer.

Thus, in a first aspect the present invention provides a pharmaceutical combination comprising:
(a) a PPAR agonist;
(b) a compound of the formula I or II

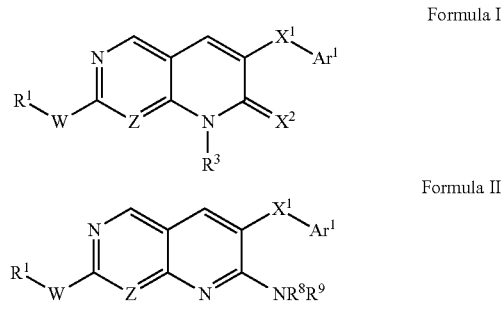

or pharmaceutically acceptable salts thereof, wherein
Z is N or CH;
W is $NR^2$;
$X^1$ is O, $NR^4$ (where $R^4$ is hydrogen or alkyl), S, or $CR^5R^6$ (where $R^5$ and $R^6$ are independently hydrogen or alkyl) or C=O;
$X^2$ is O or $NR^7$;
$Ar^1$ is aryl or heteroaryl;
$R^2$ is hydrogen, alkyl, acyl, alkoxycarbonyl, aryloxycarbonyl, heteroalkylcarbonyl, heteroalkyloxycarbonyl or —$R^{21}$-$R^{22}$ where $R^{21}$ is alkylene or —C(=O)— and $R^{22}$ is alkyl or alkoxy;
$R^1$ is hydrogen, alkyl, haloalkyl, aryl, aralkyl, heteroaryl, heteroaralkyl, cycloalkyl, cycloalkylalkyl, heteroalkyl-substituted cycloalkyl, heterosubstituted cycloalkyl, heteroalkyl, cyanoalkyl, heterocyclyl, heterocyclylalkyl, $R^{12}$—$SO_2$-heterocycloamino (where $R^{12}$ is haloalkyl, aryl, aralkyl, heteroaryl or heteroaralkyl), —$Y^1$—C(O)—$Y^2$—$R^{11}$ (where $Y^1$ and $Y^2$ are independently either absent or an alkylene group and $R^{11}$ is hydrogen, alkyl, haloalkyl, hydroxy, alkoxy, amino, monoalkylamino or dialkylamino), (heterocyclyl)(cycloalkyl)alkyl or (heterocyclyl)(heteroaryl)alkyl;
$R^3$ is hydrogen, alkyl, cycloalkyl, cycloalkylalkyl, aryl, aralkyl, haloalkyl, heteroalkyl, cyanoalkyl, alkylene-C(O)—$R^{31}$ (where $R^{31}$ is hydrogen, alkyl, hydroxy, alkoxy, amino, monoalkylamino or dialkylamino), amino, monoalkylamino, dialkylamino or $NR^{32}$—$Y^3$—$R^{33}$ (where $Y^3$ is —C(O), —C(O)O—, —C(O)$NR^{34}$, $S(O)_2$ or $S(O)_2NR^{35}$; $R^{32}$, $R^{34}$ and $R^{35}$ are independently hydrogen or alkyl; and $R^{33}$ is hydrogen, alkyl, cycloalkyl, cycloalkylalkyl, heteroalkyl or optionally substituted phenyl) or acyl;

$R^7$ is hydrogen or alkyl; and $R^8$ and $R^9$ are independently hydrogen, alkyl, aryl, aralkyl, cycloalkyl, cycloalkylalkyl, heteroalkyl, alkylsulfonyl, arylsulfonyl, —C(O)—$R^{81}$ (where $R^{81}$ is alkyl, aryl, aralkyl, cycloalkyl, cycloalkylalkyl, heteroalkyl, alkoxy, aryloxy, amino, mono- or dialkylamino, arylamino or aryl(alkyl)amino) or $R^8$ and $R^9$ together form =$CR^{82}R^{83}$ (where $R^{82}$ and $R^{83}$ are independently hydrogen, alkyl, cycloalkyl, cycloalkylalkyl or optionally substituted phenyl);

and optionally (c) one or more pharmaceutically acceptable diluents, excipients or carriers.

For the purposes of interpreting this specification, the following definitions will apply and whenever appropriate, terms used in the singular will also include the plural and vice versa. It is to be understood that the terminology used herein is for the purpose of describing particular embodiments only and is not intended to be limiting. The terms "comprising", "having", and "including" are to be construed as open-ended terms (i.e., meaning "including, but not limited to,") unless otherwise noted.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The terms "individual," "subject" or "patient" are used herein interchangeably. In certain embodiments, the subject is a mammal. Mammals include, but are not limited to primates (including human and non-human primates). In a preferred embodiment, the subject is a human.

The terms "cancer" and "cancerous" as used herein refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, cancer of the gastrointestinal (GI) tract, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

The term "metastatic cancer" as used herein means the state of cancer, e.g. the state of lung cancer or cancer of the gastrointestinal (GI) tract where the cancer cells are transmitted from the original site to one or more sites elsewhere in the body, by the blood vessels or lymphatics, to form one or more secondary tumors at one or more sites or organs besides the original site or organ.

The term "about" as used herein refers to +/−10% of a given measurement.

PPAR Agonists

The term "PPAR agonist" as used herein refers to a drug that is activating peroxisome proliferator activated receptor (PPAR) such as PPAR gamma receptor, PPAR alpha receptor, PPAR delta receptor or combinations thereof. In a preferred embodiment, the PPAR agonist according to the invention is activating PPAR gamma.

In a further embodiment, said PPAR agonist is a PPAR gamma agonist selected from a list comprising pioglitazone, troglitazone and rosiglitazone or a pharmaceutically acceptable salt thereof; or a PPAR alpha agonist selected from a list comprising fibrates such as fenofibrate (fenofibric acid), clofibrate or gemfibrozil or a pharmaceutically acceptable salt thereof; or a PPAR dual agonist (PPAR alpha/gamma or PPAR alpha/delta agonists) selected from a list comprising aleglitazar, muraglitazar, tesaglitazar, ragaglitazar, saroglitazar, GFT505 and naveglitazar or a pharmaceutically acceptable salt thereof; or a PPAR delta agonist such as GW501516 or a pharmaceutically acceptable salt thereof; or a PPAR pan agonists (PPAR alpha/delta/gamma agonist); or a selective PPAR modulator such as e.g. INT131 or a pharmaceutically acceptable salt thereof.

Usually PPAR gamma agonists, PPAR modulators, PPAR alpha agonists and/or PPAR alpha/gamma dual agonists are used in the context of the present invention. In particular PPAR gamma agonists, PPAR alpha agonists and/or PPAR alpha/gamma dual agonists, more particular PPAR gamma agonists are used in the context of the present invention.

In a preferred embodiment, the PPAR agonist according to the invention is a PPAR gamma agonist or modulator selected from the group consisting of pioglitazone, rosiglitazone, troglitazone, INT131 or a pharmaceutically acceptable salt thereof.

In an even more preferred embodiment, said PPAR agonist is a PPAR gamma agonist selected from the group consisting of pioglitazone, rosiglitazone and troglitazone or a pharmaceutically acceptable salt thereof.

In a most preferred embodiment, said PPAR agonist is pioglitazone or a pharmaceutically acceptable salt thereof, e.g. pioglitazone hydrochloride.

In a further embodiment, said PPAR agonist is a PPAR alpha agonist selected from the group consisting of fenofibrate (fenofibric acid), clofibrate and gemfibrozil, preferably fenofibrate (fenofibric acid) or a pharmaceutically acceptable salt thereof.

In yet a further embodiment, said PPAR agonist is a PPAR alpha/gamma dual agonist selected from the group consisting of aleglitazar, muraglitazar, tesaglitazar, ragaglitazar, saroglitazar, GFT505 and naveglitazar or a pharmaceutically acceptable salt thereof, preferably muraglitazar or tesaglitazar or a pharmaceutically acceptable salt thereof.

Pioglitazone is described e.g. in U.S. Pat. No. 4,687,777 or in Dormandy J A, Charbonnel B, Eckland D J, Erdmann E, Massi-Benedetti M, Moules I K, Skene A M, Tan M H, Lefèbvre PJ, Murray G D, Standl E, Wilcox R G, Wilhelmsen L, Betteridge J, Birkeland K, Golay A, Heine R J, Korányi L, Laakso M, Mokán M, Norkus A, Pirags V, Podar T, Scheen A, Scherbaum W, Schernthaner G, Schmitz O, Skrha J, Smith U, Taton J; PROactive investigators. Lancet.

2005 Oct. 8; 366(9493): 1279-89, and is represented by the structural formula indicated below:

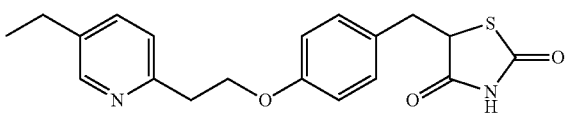 [SMILES: CCc1ccc(CCOc2ccc(CC3SC(=O)NC3=O)cc2)nc1]

Troglitazone is described e.g. in Florez J C, Jablonski K A, Sun M W, Bayley N, Kahn S E, Shamoon H, Hamman R F, Knowler W C, Nathan D M, Altshuler D; Diabetes Prevention Program Research Group. J Clin Endocrinol Metab. 2007 April; 92(4):1502-9 and is represented by the structural formula indicated below:

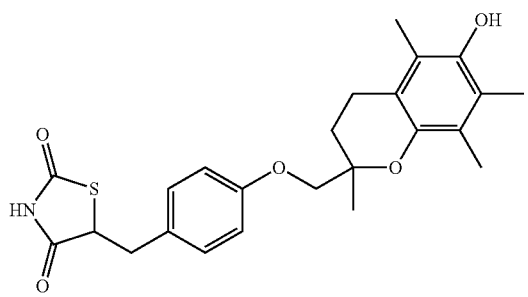 [SMILES: Cc1c(C)c2c(c(C)c1O)CCC(C)(COc1ccc(CC3SC(=O)NC3=O)cc1)O2]

Rosiglitazone is described e.g. in Nissen S E, Wolski K. N Engl J Med. 2007 Jun. 14; 356(24):2457-71. Erratum in: N Engl J Med. 2007 Jul. 5; 357(1):100. Fenofibrate is described e.g. in Bonds D E, Craven T E, Buse J, Crouse J R, Cuddihy R, Elam M, Ginsberg H N, Kirchner K, Marcovina S, Mychaleckyj J C, O'Connor P J, Sperl-Hillen J A. Diabetologia. 2012 June; 55(6):1641-50 and is represented by the structural formula indicated below:

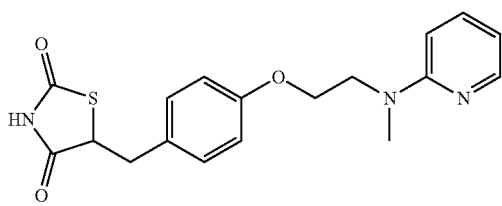 [SMILES: CN(CCOc1ccc(CC2SC(=O)NC2=O)cc1)c1ccccn1]

Clofibrate is described e.g. in Rabkin S W, Hayden M, Frohlich J. Atherosclerosis. 1988 October; 73(2-3):233-40 and is represented by the structural formula indicated below:

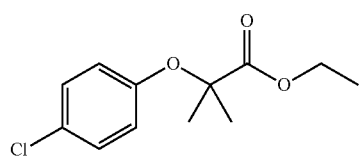 [SMILES: CCOC(=O)C(C)(C)Oc1ccc(Cl)cc1]

Fenofibrate (fenofibric acid) is described e.g. in Schima S M, Maciejewski S R, Hilleman D E, Williams M A, Mohiuddin S M. Expert Opin Pharmacother. 2010 April; 11(5): 731-8 and is represented by the structural formula indicated below:

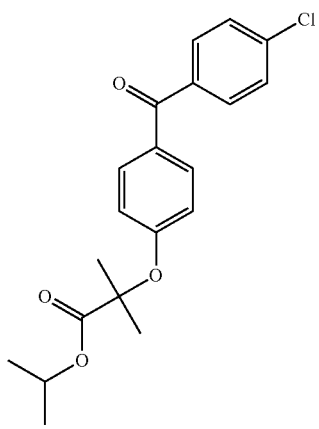 [SMILES: CC(C)OC(=O)C(C)(C)Oc1ccc(C(=O)c2ccc(Cl)cc2)cc1]

Gemfibrozil is described e.g. in Adabag A S, Mithani S, Al Aloul B, Collins D, Bertog S, Bloomfield H E; Veterans Affairs High-Density Lipoprotein Cholesterol Intervention Trial Study Group. Am Heart J. 2009 May; 157(5):913-8 and is represented by the structural formula indicated below:

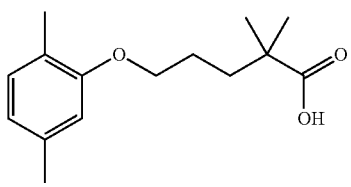 [SMILES: Cc1ccc(C)c(OCCCC(C)(C)C(=O)O)c1]

Aleglitazar is described e.g. in Lincoff A M, Tardif J C, Schwartz G G, Nicholls S J, Rydén L, Neal B, Malmberg K, Wedel H, Buse J B, Henry R R, Weichert A, Cannata R, Svensson A, Volz D, Grobbee D E; AleCardio Investigators. JAMA. 2014 Apr. 16; 311(15):1515-25 and is represented by the structural formula indicated below:

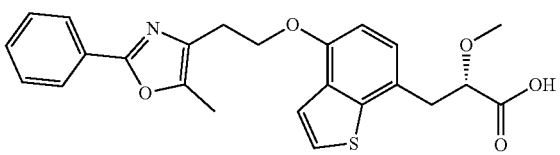 [SMILES: CO[C@@H](Cc1ccc(OCCc2nc(-c3ccccc3)oc2C)c2ccsc12)C(=O)O]

Muraglitazar is described e.g. in Fernandez M, Gastaldelli A, Triplitt C, Hardies J, Casolaro A, Petz R, Tantiwong P, Musi N, Cersosimo E, Ferrannini E, DeFronzo R A. Diabetes Obes Metab. 2011 October; 13(10):893-902 and is represented by the structural formula indicated below:

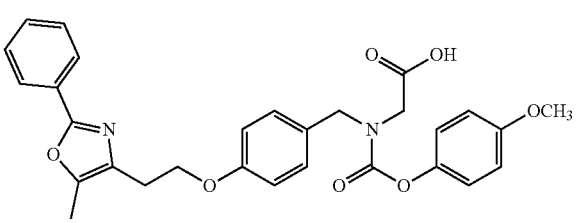 [SMILES: COc1ccc(OC(=O)N(CC(=O)O)Cc2ccc(OCCc3nc(-c4ccccc4)oc3C)cc2)cc1]

Tesaglitazar is described e.g. in Bays H, McElhattan J, Bryzinski B S; GALLANT 6 Study Group. Diab Vasc Dis Res. 2007 September; 4(3):181-93 and is represented by the structural formula indicated below:

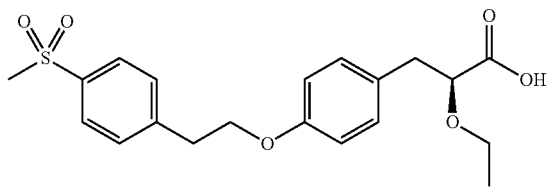 [SMILES: CCO[C@@H](Cc1ccc(OCCc2ccc(S(C)(=O)=O)cc2)cc1)C(=O)O]

Ragaglitazar is described e.g. in Saad M F, Greco S, Osei K, Lewin A J, Edwards C, Nunez M, Reinhardt R R; Ragaglitazar Dose-Ranging Study Group. Diabetes Care. 2004 June; 27(6): 1324-9 and is represented by the structural formula indicated below:

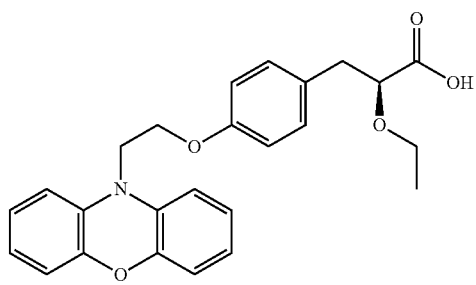 [SMILES: CCO[C@@H](Cc1ccc(OCCN2c3ccccc3Oc3ccccc32)cc1)C(=O)O]

Saroglitazar is described e.g. in Agrawal R. Curr Drug Targets. 2014 February; 15(2): 151-5. and is represented by the structural formula indicated below:

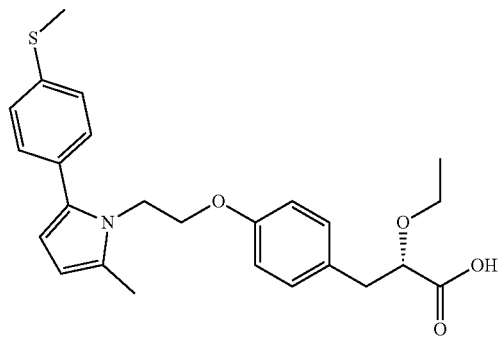 [SMILES: CCO[C@@H](Cc1ccc(OCCn2c(C)ccc2-c2ccc(SC)cc2)cc1)C(=O)O]

Naveglitazar is described e.g. in Ahlawat P, Srinivas N R. Eur J Drug Metab Pharmacokinet. 2008 July-September; 33(3):187-90. GW501516 is described e.g. in Wang X, Sng M K, Foo S, Chong H C, Lee W L, Tang M B, Ng K W, Luo B, Choong C, Wong M T, Tong B M, Chiba S, Loo S C, Zhu P, Tan N S. J Control Release. 2015 Jan. 10; 197:138-47 and is represented by the structural formula indicated below:

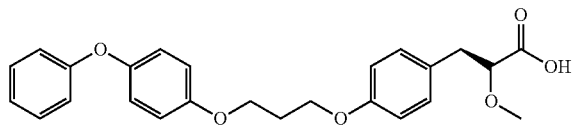

GFT505 is described e.g. in Cariou B, Staels B. Expert Opin Investig Drugs. 2014 October; 23(10): 1441-8 and is represented by the structural formula indicated below:

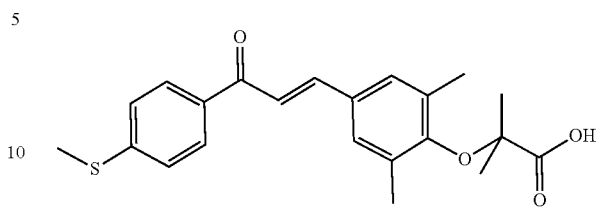

INT131 is described e.g. in. Taygerly J P, McGee L R, Rubenstein S M, Houze J B, Cushing T D, Li Y, Motani A, Chen J L, Frankmoelle W, Ye G, Learned M R, Jaen J, Miao S, Timmermans P B, Thoolen M, Keamey P, Flygare J, Beckmann H, Weiszmann J, Lindstrom M, Walker N, Liu J, Biermann D, Wang Z, Hagiwara A, Iida T, Aramaki H, Kitao Y, Shinkai H, Furukawa N, Nishiu J, Nakamura M. Bioorg Med Chem. 2013 Feb. 15; 21(4):979-92 and is represented by the structural formula indicated below:

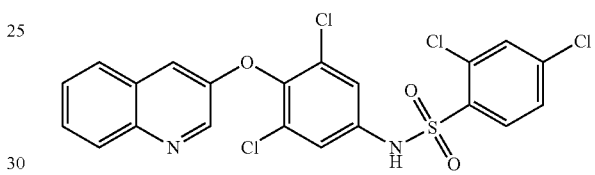

PPAR activation by the PPAR agonist is usually strong in the low nanomolar range to low micromolar range, e.g in a range of 0.1 nM to 100 µM. In some embodiments the PPAR activation is weak or partial, i.e. a PPAR agonist is used in the methods of the present invention which yields maximal activation of PPAR-receptor in a reporter assay system of 10% to 100% compared to a reference PPAR agonist which is known to causes a maximum PPAR activation.

P38 Inhibitors

The term "p38 inhibitor" as used herein refers to a drug that is inhibiting a p38 mitogen-activated protein (MAP) kinase, such as p38-α (MAPK14), p38-β (MAPK11), p38-γ (MAPK12/ERK6), and/or p38-δ (MAPK13/SAPK4).

The term "p38 inhibitor" includes p38 inhibitors such as the compounds of formulae I and II

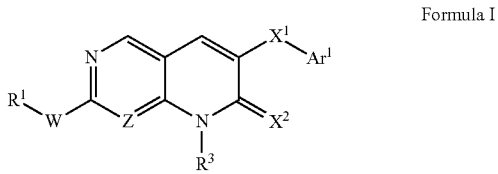

Formula I

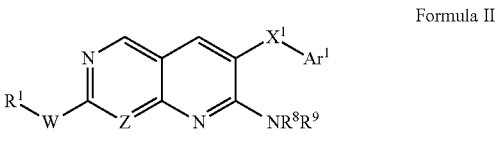

Formula II or pharmaceutically acceptable salts thereof, wherein

Z is N or CH;

W is $NR^2$;

$X^1$ is O, $NR^4$ (where $R^4$ is hydrogen or alkyl), S, or $CR^5R^6$ (where $R^5$ and $R^6$ are independently hydrogen or alkyl) or C=O;

$X^2$ is O or $NR^7$;

$Ar^1$ is aryl or heteroaryl;

$R^2$ is hydrogen, alkyl, acyl, alkoxycarbonyl, aryloxycarbonyl, heteroalkylcarbonyl, heteroalkyloxycarbonyl or —$R^{21}$-$R^{22}$ where $R^{21}$ is alkylene or —C(=O)— and $R^{22}$ is alkyl or alkoxy;

$R^1$ is hydrogen, alkyl, haloalkyl, aryl, aralkyl, heteroaryl, heteroaralkyl, cycloalkyl, cycloalkylalkyl, heteroalkyl-substituted cycloalkyl, heterosubstituted cycloalkyl, heteroalkyl, cyanoalkyl, heterocyclyl, heterocyclylalkyl, $R^{12}$—$SO_2$-heterocycloamino (where $R^{12}$ is haloalkyl, aryl, aralkyl, heteroaryl or heteroaralkyl), —$Y^1$—C(O)—$Y^2$—$R^{11}$ (where $Y^1$ and $Y^2$ are independently either absent or an alkylene group and $R^{11}$ is hydrogen, alkyl, haloalkyl, hydroxy, alkoxy, amino, monoalkylamino or dialkylamino), (heterocyclyl)(cycloalkyl)alkyl or (heterocyclyl)(heteroaryl)alkyl;

$R^3$ is hydrogen, alkyl, cycloalkyl, cycloalkylalkyl, aryl, aralkyl, haloalkyl, heteroalkyl, cyanoalkyl, alkylene-C(O)—$R^{31}$ (where $R^{31}$ is hydrogen, alkyl, hydroxy, alkoxy, amino, monoalkylamino or dialkylamino), amino, monoalkylamino, dialkylamino or $NR^{32}$—$Y^3$—$R^{33}$ (where $Y^3$ is —C(O), —C(O)O—, —C(O)$NR^{34}$, $S(O)_2$ or $S(O)_2 NR^{35}$; $R^{32}$, $R^{34}$ and $R^{35}$ are independently hydrogen or alkyl; and $R^{33}$ is hydrogen, alkyl, cycloalkyl, cycloalkylalkyl, heteroalkyl or optionally substituted phenyl) or acyl;

$R^7$ is hydrogen or alkyl; and $R^8$ and $R^9$ are independently hydrogen, alkyl, aryl, aralkyl, cycloalkyl, cycloalkylalkyl, heteroalkyl, alkylsulfonyl, arylsulfonyl, —C(O)—$R^{81}$ (where $R^{81}$ is alkyl, aryl, aralkyl, cycloalkyl, cycloalkylalkyl, heteroalkyl, alkoxy, aryloxy, amino, mono- or dialkylamino, arylamino or aryl(alkyl)amino) or $R^8$ and $R^9$ together form =$CR^{82}R^{83}$ (where $R^{82}$ and $R^{83}$ are independently hydrogen, alkyl, cycloalkyl, cycloalkylalkyl or optionally substituted phenyl).

Unless otherwise stated, the following terms used in the specification and claims have the meanings given below:

"Acyl" means a radical —C(O)R, where R is hydrogen, alkyl, cycloalkyl, cycloalkylalkyl, phenyl or phenylalkyl wherein alkyl, cycloalkyl, cycloalkylalkyl, and phenylalkyl are as defined herein. Representative examples include, but are not limited to formyl, acetyl, cylcohexylcarbonyl, cyclohexylmethylcarbonyl, benzoyl, benzylcarbonyl, and the like.

"Acylamino" means a radical-NR'C(O)R, where R' is hydrogen or alkyl, and R is hydrogen, alkyl, cycloalkyl, cycloalkylalkyl, phenyl or phenylalkyl wherein alkyl, cycloalkyl, cycloalkylalkyl, and phenylalkyl are as defined herein. Representative examples include, but are not limited to formylamino, acetylamino, cylcohexylcarbonylamino, cyclohexylmethyl-carbonylamino, benzoylamino, benzylcarbonylamino, and the like.

"Alkoxy" means a radical —OR where R is an alkyl as defined herein. Examples are methoxy, ethoxy, propoxy, butoxy and the like.

"Alkyl" means a linear saturated monovalent hydrocarbon radical of one to six carbon atoms or a branched saturated monovalent hydrocarbon radical of three to six carbon atoms. Examples are methyl, ethyl, propyl, 2-propyl, n-butyl, iso-butyl, tert-butyl, pentyl, and the like.

"Alkylene" means a linear saturated divalent hydrocarbon radical of one to six carbon atoms or a branched saturated divalent hydrocarbon radical of three to six carbon atoms. Examples are methylene, ethylene, 2,2-dimethylethylene, propylene, 2-methylpropylene, butylen, pentylene, and the like.

"Aryl" means a monovalent monocyclic or bicyclic aromatic hydrocarbon radical which is optionally substituted independently with one or more substituents, preferably one, two or three substituents preferably selected from the group consisting of alkyl, hydroxy, alkoxy, haloalkyl, haloalkoxy, Y—C(O)—R (where Y is absent or an alkylene group and R is hydrogen, alkyl, haloalkyl, haloalkoxy, hydroxy, alkoxy, amino, monoalkylamino or dialkylamino), heteroalkyl, heteroalkyloxy, heteroalkylamino, halo, nitro, cyano, amino, monoalkylamino, dialkylamino, alkylsulfonylamino, heteroalkylsulfonylamino, sulfonamido, methylenedioxy, ethylenedioxy, heterocyclyl or heterocyclylalkyl. More specifically the term aryl includes, but is not limited to, phenyl, chlorophenyl, methoxyphenyl, 2-fluorophenyl, 2,4-difluorophenyl, 1-naphthyl, 2-naphthyl, and the derivatives thereof. In a preferred embodiment, the term aryl refers to 2,4-difluorophenyl.

"Aryloxy" means a radical —OR where R is an aryl as defined herein, e. g. phenoxy.

"Aryloxycarbonyl" means a radical R—C(=O)— where R is aryloxy, e.g. phenoxycarbonyl.

"Cycloalkyl" refers to a saturated monovalent cyclic hydrocarbon radical of three to seven ring carbons or more specifically those of the specific compounds listed in the enclosed tables or being described in the examples. It is understand that these radicals can be grouped also in a group covering only such radicals but of the first or the second priority application or of both priority applications e. g., cyclopropyl, cyclobutyl, cyclohexyl, 4-methyl-cyclohexyl, and the like.

"Cycloalkylalkyl" means a radical —$R^a R^b$ where $R^a$ is an alkylene group and $R^b$ is cycloalkyl group as defined herein, e. g., cyclohexylmethyl, and the like.

"Substituted cycloalkyl" means a cycloalkyl radical as defined herein with one, two or three (preferably one) ring hydrogen atoms independently replaced by cyano or —Y—C(O)R (where Y is absent or an alkylene group and R is hydrogen, alkyl, haloalkyl, hydroxy, alkoxy, amino, monoalkylamino, dialkylamino, or optionally substituted phenyl) or more specifically those of the specific compounds listed in the enclosed tables or being described in the examples.

"Dialkylamino" means a radical —NRR' where R and R' independently represent an alkyl, hydroxyalkyl, cycloalkyl, or cycloalkylalkyl group as defined herein. Representative examples include, but are not limited to dimethylamino, methylethylamino, di(1-methylethyl)amino, (methyl)(hydroxymethyl)amino, (cyclohexyl)(methyl)amino, (cyclohexyl)(ethyl)amino, (cyclohexyl)(propyl)amino, (cyclohexylmethyl)(methyl)amino, (cyclohexylmethyl)(ethyl)amino, and the like.

"Halo" means fluoro, chloro, bromo, or iodo, preferably fluoro and chloro.

"Haloalkyl" means alkyl substituted with one or more same or different halo atoms, e. g. —$CH_2Cl$, —$CF_3$, —$CH_2CF_3$, —$CH_2CCl_3$, and the like.

"Heteroalkyl" means an alkyl radical as defined herein wherein one, two or three hydrogen atoms have been replaced with a substituent independently selected from the group consisting of —$OR^a$, —$N(O)_n R^b R^c$ (where n is 0 or 1 if $R^b$ and $R^c$ are both independently alkyl, cycloalkyl or cycloalkylalkyl, and 0 if not) and —$S(O)_n R^d$ (where n is an integer from 0 to 2), with the understanding that the point of attachment of the heteroalkyl radical is through a carbon atom, wherein $R^a$ is hydrogen, acyl, alkoxycarbonyl, alkyl, cycloalkyl, or cycloalkylalkyl; $R^b$ and $R^c$ are independently of each other hydrogen, acyl, alkoxycarbonyl, alkyl, cycloalkyl, cycloalkylalkyl, alkylsulfonyl, aminosulfonyl, mono- or dialkylaminosulfonyl, aminoalkyl, mono- or di-alkylaminoalkyl, hydroxyalkyl, alkoxyalkyl, hydroxyalkylsulfonyl or alkoxyalkylsulfonyl; and when n is 0, $R^d$ is hydrogen, alkyl, cycloalkyl, cycloalkylalkyl or optionally substituted phenyl, and when n is 1 or 2, $R^d$ is alkyl, cycloalkyl, cycloalkylalkyl, optionally substituted phenyl, amino, acylamino, monoalkylamino, or dialkylamino. Representative examples include, but are not limited to, 2-hydroxyethyl, 2-hydroxy-propyl, 3-hydroxypropyl, 2-hydroxy-1-hydroxymethylethyl, 2-hydroxy-1-methylethyl, 2,3-dihydroxypropyl, 1-hydroxymethylethyl, 3-hydroxybutyl, 2,3-dihydroxybutyl, 2-hydroxy-1-methylpropyl, 3-hydroxy-1-(2-hydroxyethyl)-propyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like, preferably 2-hydroxy-propyl, 3-hydroxy-1-(2-hydroxyethyl)-propyl or 2-hydroxy-1-methylethyl.

"Heteroalkylcarbonyl" means the group $R^a$—C(=O)—, where $R^a$ is a heteroalkyl group. Representative examples include acetyloxymethylcarbonyl, aminomethylcarbonyl, 4-acetyloxy-2,2-dimethyl-butan-2-oyl, 2-amino-4-methyl-pentan-2-oyl, and the like.

"Heteroalkyloxy" means the group $R^a$—O—, where $R^a$ is a heteroalkyl group. Representative examples include (Me-C(=O)—O—CH$_2$—O—, and the like.

"Heteroalkyloxycarbonyl" means the group $R^a$—C(=O), where $R^a$ is heteroalkyloxy. Representative examples include 1-acetyloxy-methoxycarbonyl (Me-C(=O)—OCH$_2$—O—C(=O)—) and the like.

"Heteroaryl" means a monovalent monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one or more substituents, preferably one or two substituents, selected from alkyl, haloalkyl, heteroalkyl, hydroxy, alkoxy, halo, nitro or cyano. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, imidazo[1,2-a]-pyridinyl, imidazo[2,1-b]thiazolyl, and the derivatives thereof.

"Heteroaralkyl" means a radical —$R^aR^b$ where $R^a$ is an alkylene group and $R^b$ is a heteroaryl group, e. g. pyridin-3-ylmethyl, imidazolylethyl, pyridinylethyl, 3-(benzofuran-2-yl)propyl, and the like.

"Heteroalkylsubstituted cycloalkyl" means a cycloalkyl radical as defined herein wherein one, two or three hydrogen atoms in the cycloalkyl radical have been replaced with a heteroalkyl group with the understanding that the heteroalkyl radical is attached to the cycloalkyl radical via a carbon-carbon bond. Representative examples include, but are not limited to, 1-hydroxymethylcyclopentyl, 2-hydroxymethylcyclohexyl, and the like.

"Heterosubstituted cycloalkyl" means a cycloalkyl radical as defined herein wherein one, two or three hydrogen atoms in the cycloalkyl radical have been replaced with a substituent independently selected from the group consisting of hydroxy, alkoxy, amino, acylamino, monoalkylamino, dialkylamino, oxo(C=O), imino, hydroximino (=NOH), NR'SO$_2$R$^d$ (where R' is hydrogen or alkyl and $R^d$ is alkyl, cycloalkyl, hydroxyalkyl, amino, monoalkylamino or dialkylamino), —X—Y—C(O)R (where X is O or NR', Y is alkylene or absent, R is hydrogen, alkyl, haloalkyl, alkoxy, amino, monoalkylamino, dialkylamino, or optionally substituted phenyl, and R' is H or alkyl), or —S(O)$_n$R (where n is an integer from 0 to 2) such that when n is 0, R is hydrogen, alkyl, cycloalkyl, cycloalkylalkyl optionally substituted phenyl or thienyl, and when n is 1 or 2, R is alkyl, cycloalkyl, cycloalkylalkyl, optionally substituted phenyl, thienyl, amino, acylamino, monoalkylamino or dialkylamino. Representative examples include, but are not limited to, 2-, 3-, or 4-hydroxycyclohexyl, 2-, 3-, or 4-aminocyclohexyl, 2-, 3-, or 4-methanesulfonamido-cyclohexyl, and the like, preferably 4-hydroxycyclohexyl, 2-aminocyclohexyl or 4-methanesulfonamido-cyclohexyl.

"Heterosubstituted cycloalkyl-alkyl" means a radical $R^aR^b$— where $R^a$ is a heterosubstituted cycloalkyl radical and $R^b$ is an alkylene radical.

"Heterocycloamino" means a saturated monovalent cyclic group of 4 to 8 ring atoms, wherein one ring atom is N and the remaining ring atoms are C. Representative examples include piperidine and pyrrolidine.

"Heterocyclyl" means a saturated or unsaturated non-aromatic cyclic radical of 3 to 8 ring atoms in which one or two ring atoms are heteroatoms selected from N, O, or S(O)$_n$ (where n is an integer from 0 to 2), the remaining ring atoms being C, where one or two C atoms may optionally be replaced by a carbonyl group. The heterocyclyl ring may be optionally substituted independently with one, two, or three substituents selected from alkyl, haloalkyl, heteroalkyl, halo, nitro, cyano, cyanoalkyl, hydroxy, alkoxy, amino, monoalkylamino, dialkylamino, aralkyl, —(X)$_n$—C(O)R (where X is O or NR', n is 0 or 1, R is hydrogen, alkyl, haloalkyl, hydroxy (when n is 0), alkoxy, amino, monoalkylamino, dialkylamino, or optionally substituted phenyl, and R' is H or alkyl), -alkylene-C(O)R$^a$ (where R$^a$ is alkyl, OR or NR'R" and R is hydrogen, alkyl or haloalkyl, and R' and R" are independently hydrogen or alkyl), or —S(O)$_n$R (where n is an integer from 0 to 2) such that when n is 0, R is hydrogen, alkyl, cycloalkyl, or cycloalkylalkyl, and when n is 1 or 2, R is alkyl, cycloalkyl, cycloalkylalkyl, amino, acylamino, monoalkylamino, dialkylamino or heteroalkyl. More specifically the term heterocyclyl includes, but is not limited to, tetrahydropyranyl, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, 4-(1,1-dioxotetrahydro-2H-thiopyranyl), pyrrolinyl, imidazolinyl, N-methanesulfonyl-piperidin-4-yl, and the derivatives thereof.

"Heterocyclylalkyl" means a radical —$R^aR^b$ where $R^a$ is an alkylene group and $R^b$ is a heterocyclyl group as defined above, e. g. tetrahydropyran-2-ylmethyl, 2- or 3-piperidinylmethyl, 3-(4-methyl-piperazin-1-yl)propyl and the like.

"(Heterocyclyl)(cycloalkyl)alkyl" means an alkyl radical wherein two hydrogen atoms have been replaced with a heterocyclyl group and a cycloalkyl group.

"(Heterocyclyl)(heteroaryl)alkyl" means an alkyl radical wherein two hydrogen atoms have been replaced with a heterocycyl group and a heteroaryl group.

"Heterocyclyl spiro cycloalkyl" means a spiro radical consisting of a cycloalkyl ring and a heterocyclic ring with each ring having 5 to 8 ring atoms and the two rings having only one carbon atom in common, with the understanding that the point of attachment of the heterocyclyl spiro cycloalkyl radical is via the cycloalkyl ring. The spiro radical is formed when two hydrogen atoms from the same carbon atom of the cycloalkyl radical are replaced with a heterocyclyl group as defined herein, and may be optionally substituted with alkyl, hydroxy, hydroxyalkyl, or oxo. Examples include, but are not limited to, 1,4-dioxaspiro[4.5]decan-8-yl, 1,3-diazaspiro[4.5]decan-8-yl, 2,4-dione-1,3diaza-spiro[4.5]decan-8-yl, 1,5-dioxa-spiro [5.5]undecan-9-yl, (3-hydroxymethyl-3-methyl)-1,5-dioxaspiro[5.5]undecan-9-yl, and the like.

"Hydroxyalkyl" means an alkyl radical as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl, preferably 2-hydroxyethyl, 2,3-dihydroxypropyl and 1-(hydroxymethyl)2-hydroxyethyl. Accordingly, as used herein, the term "hydroxyalkyl" is used to define a subset of heteroalkyl groups.

"Monoalkylamino" means a radical —NHR where R is an alkyl, hydroxyalkyl, cycloalkyl, or cycloalkylalkyl group as defined above, e. g. methylamino, (1-methylethyl) amino, hydroxymethylamino, cyclohexylamino, cyclohexylmethylamino, cyclohexylethylamino, and the like.

"Optionally substituted phenyl" means a phenyl ring which is optionally substituted independently with one or more substituents, preferably one or two substituents selected from the group consisting of alkyl, hydroxy, alkoxy, haloalkyl, haloalkoxy, heteroalkyl, halo, nitro, cyano, amino, methylenedioxy, ethylenedioxy, and acyl.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxy-benzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-enel-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e. g. an alkaline metal ion, an alkaline earth metal ion, or an aluminum ion; or coordinates with an organic base such as ethanolamine, diethanolamine, triethanolamine, tromethamine, N-methylglucamine, and the like.

In one embodiment, the p38 inhibitor according to the invention is a compound of formula I

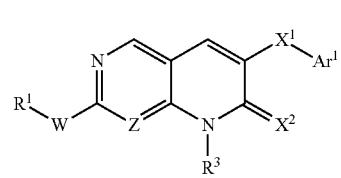

Formula I or pharmaceutically acceptable salts thereof, wherein

Z is N or CH;

W is $NR^2$;

$X^1$ is O, $NR^4$ (where $R^4$ is hydrogen or alkyl), S, or $CR^5R^6$ (where $R^5$ and $R^6$ are independently hydrogen or alkyl) or C=O;

$X^2$ is O or $NR^7$;

$Ar^1$ is aryl or heteroaryl;

$R^2$ is hydrogen, alkyl, acyl, alkoxycarbonyl, aryloxycarbonyl, heteroalkylcarbonyl, heteroalkyloxycarbonyl or —$R^{21}$-$R^{22}$ where $R^{21}$ is alkylene or —C(=O)— and $R^{22}$ is alkyl or alkoxy;

$R^1$ is hydrogen, alkyl, haloalkyl, aryl, aralkyl, heteroaryl, heteroaralkyl, cycloalkyl, cycloalkylalkyl, heteroalkyl-substituted cycloalkyl, heterosubstituted cycloalkyl, heteroalkyl, cyanoalkyl, heterocyclyl, heterocyclylalkyl, $R^{12}$—$SO_2$-heterocycloamino (where $R^{12}$ is haloalkyl, aryl, aralkyl, heteroaryl or heteroaralkyl), —$Y^1$—C(O)—$Y^2$—$R^{11}$ (where $Y^1$ and $Y^2$ are independently either absent or an alkylene group and $R^{11}$ is hydrogen, alkyl, haloalkyl, hydroxy, alkoxy, amino, monoalkylamino or dialkylamino), (heterocyclyl)(cycloalkyl)alkyl or (heterocyclyl)(heteroaryl)alkyl;

$R^3$ is hydrogen, alkyl, cycloalkyl, cycloalkylalkyl, aryl, aralkyl, haloalkyl, heteroalkyl, cyanoalkyl, alkylene-C(O)—$R^{31}$ (where $R^{31}$ is hydrogen, alkyl, hydroxy, alkoxy, amino, monoalkylamino or dialkylamino), amino, monoalkylamino, dialkylamino or $NR^{32}$—$Y^3$—$R^{33}$ (where $Y^3$ is —C(O), —C(O)O—, —C(O)$NR^{34}$, $S(O)_2$ or $S(O)_2NR^{35}$; $R^{32}$, $R^{34}$ and $R^{35}$ are independently hydrogen or alkyl; and $R^{33}$ is hydrogen, alkyl, cycloalkyl, cycloalkylalkyl, heteroalkyl or optionally substituted phenyl) or acyl; and $R^7$ is hydrogen or alkyl and optionally one or more pharmaceutically acceptable diluents, excipients or carriers.

In a further embodiment, the p38 inhibitor according to the invention is a compound of formula I wherein $X^1$ is $NR^4$ and $X^2$ is $NR^7$ or $X^1$ and $X^2$ are each 0, wherein $R^4$ and $R^7$ are as defined above.

In a further embodiment, the p38 inhibitor according to the invention is a compound of formula I wherein W is $NR^2$, wherein $R^2$ is hydrogen, alkyl, acyl or alkoxycarbonyl, preferably hydrogen or alkyl, more preferably hydrogen.

In yet a further embodiment, the p38 inhibitor according to the invention is a compound of formula I wherein $R^1$ is hydrogen, alkyl, haloalkyl, cycloalkyl, cycloalkylalkyl, heteroalkylsubstituted cycloalkyl, heterosubstituted cycloalkyl, heteroalkyl, cyanoalkyl, heterocyclyl, heterocyclylalkyl or (heterocyclyl)(cycloalkyl)alkyl.

In yet a further embodiment, the p38 inhibitor according to the invention is a compound of formula I wherein $R^1$ is hydrogen, alkyl, haloalkyl, heteroalkyl or cyanoalkyl.

In yet a further embodiment, the p38 inhibitor according to the invention is a compound of formula I wherein $R^1$ is cycloalkyl, cycloalkylalkyl, heteroalkylsubstituted cycloalkyl, heterosubstituted cycloalkyl, heterocyclyl, heterocyclylalkyl or (heterocyclyl)(cycloalkyl)alkyl.

In yet a further embodiment, the p38 inhibitor according to the invention is a compound of formula I wherein $R^3$ is hydrogen, alkyl, cycloalkyl, cycloalkylalkyl, haloalkyl, heteroalkyl, cyanoalkyl, alkylene-C(O)—$R^{31}$ (where $R^{31}$ is hydrogen, alkyl, hydroxy, alkoxy, amino, monoalkylamino or dialkylamino) or acyl.

In yet a further embodiment, the p38 inhibitor according to the invention is a compound of formula I wherein $R^3$ is hydrogen, alkyl, haloalkyl, heteroalkyl, cyanoalkyl, cycloalkyl or cycloalkylalkyl.

In yet a further embodiment, the p38 inhibitor according to the invention is a compound of formula I wherein $R^3$ is hydrogen, alkyl, haloalkyl, heteroalkyl or cyanoalkyl.

In yet a further embodiment, the p38 inhibitor according to the invention is a compound of formula I wherein $R^3$ is cycloalkyl or cycloalkylalkyl.

In yet a further embodiment, the p38 inhibitor according to the invention is a compound of formula I wherein $X^1$ and $X^2$ are both O.

In yet a further embodiment, the p38 inhibitor according to the invention is a compound of formula I wherein $R^1$ is alkyl or heteroalkyl.

In yet a further embodiment, the p38 inhibitor according to the invention is a compound of formula I wherein $R^1$ is heteroalkyl, preferably 3-hydroxy-1-(2-hydroxyethyl)-propyl or 2-hydroxy-1-methylethyl.

In yet a further embodiment, the p38 inhibitor according to the invention is a compound of formula I wherein $R^3$ is alkyl or heteroalkyl.

In yet a further embodiment, the p38 inhibitor according to the invention is a compound of formula I wherein $R^3$ is alkyl, preferably methyl.

In yet a further embodiment, the p38 inhibitor according to the invention is a compound of formula I wherein $R^3$ is heteroalkyl, preferably 2-hydroxy-propyl.

In yet a further embodiment, the p38 inhibitor according to the invention is a compound of formula I wherein W is NH.

In yet a further embodiment, the p38 inhibitor according to the invention is a compound of formula I wherein Z is N.

In yet a further embodiment, the p38 inhibitor according to the invention is a compound of formula I wherein $Ar^1$ is aryl, preferably substituted aryl, more preferably aryl substituted with two halo substituents, most preferably aryl substituted with two halo substituents in ortho and para position.

In yet a further embodiment, the p38 inhibitor according to the invention is a compound of formula I wherein $X^1$ is $NR^4$ and $X^2$ is $NR^7$ or $X^1$ and $X^2$ are each 0, wherein $R^4$ and $R^7$ are as defined above; and wherein $R^1$ is hydrogen, alkyl, haloalkyl, cycloalkyl, cycloalkylalkyl, heteroalkylsubstituted cycloalkyl, heterosubstituted cycloalkyl, heteroalkyl, cyanoalkyl, heterocyclyl, heterocyclylalkyl or (heterocyclyl)(cycloalkyl)alkyl; and wherein $R^3$ is hydrogen, alkyl, cycloalkyl, cycloalkylalkyl, haloalkyl, heteroalkyl, cyanoalkyl, alkylene-C(O)—$R^{31}$ (where $R^{31}$ is hydrogen, alkyl, hydroxy, alkoxy, amino, monoalkylamino or dialkylamino) or acyl; and wherein W is $NR^2$, wherein $R^2$ is hydrogen, alkyl, acyl or alkoxycarbonyl; and wherein $Ar^1$ is aryl; and wherein Z is N.

In a preferred embodiment, the p38 inhibitor according to the invention is a compound of formula I wherein $X^1$ and $X^2$ are each O and wherein Z is N and wherein W is NH and wherein $Ar^1$ is substituted aryl and wherein $R^1$ is heteroalkyl and wherein $R^3$ is alkyl or heteroalkyl.

In a particularly preferred embodiment, the p38 inhibitor according to the invention is pamapimod, having the chemical name 6-(2,4-Difluorophenoxy)-2-[3-hydroxy-1-(2-hydroxyethyl)-propylamino]-8-methyl-8H-pyrido[2,3-d]pyrimidin-7-one and the chemical formula III or a pharmaceutically acceptable salt thereof.

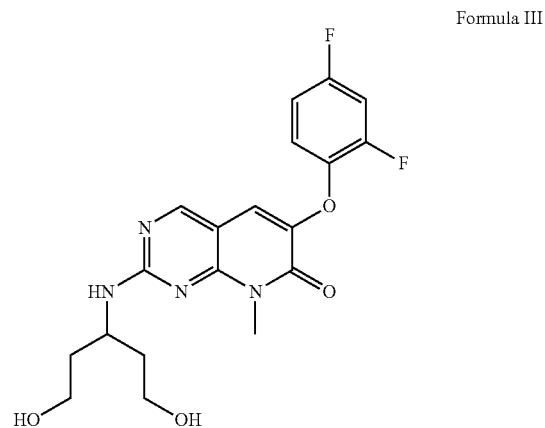 [SMILES: Cn1c(=O)c(Oc2ccc(F)cc2F)cc2cnc(NC(CCO)CCO)nc21]

Formula III

In yet another preferred embodiment, the p38 inhibitor according to the invention is R9111, having the chemical name 6-(2,4-Difluorophenoxy)-2-[(S)-2-hydroxy-1-methylethylamino]-8-[(S)-2-hydroxy-propyl]-8H-pyrido[2,3-d]pyrimidin-7-one and the chemical formula IV or a pharmaceutically acceptable salt thereof.

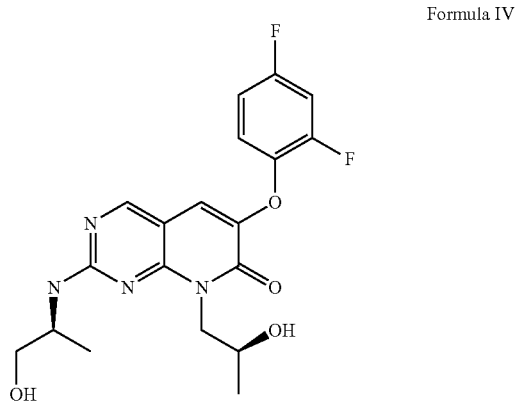 [SMILES: C[C@H](O)Cn1c(=O)c(Oc2ccc(F)cc2F)cc2cnc(N[C@@H](C)CO)nc21]

Formula IV

In yet another preferred embodiment, the p38 inhibitor according to the invention is selected from the group consisting of pamapimod, losmapimod, dilmapimod, AZD7624, ARRY-371797, LY2228820, R9111, PH-797804, BIRB 796, VX-702, VX-745 SB 239063, SB202190, SCIO 469, and BMS 582949 or a pharmaceutically acceptable salt thereof. In a more preferred embodiment, the p38 inhibitor according to the invention is selected from the group consisting of pamapimod, losmapimod, dilmapimod, ARRY-371797, LY2228820, R9111, PH-797804, BIRB 796, VX-702, VX-745 SB 239063, SB202190, SCIO 469, and BMS 582949 or a pharmaceutically acceptable salt thereof.

Pamapimod and its synthesis are described e.g. in WO2008/151992 and in WO2002/064594 and in e.g. Hill R J, Dabbagh K, Phippard D, Li C, Suttmann R T, Welch M, Papp E, Song K W, Chang K C, Leaffer D, Kim Y-N, Roberts R T, Zabka T S, Aud D, Dal Porto J, Manning A M, Peng S L, Goldstein D M, and Wong B R; Pamapimod, a Novel p38 Mitogen-Activated Protein Kinase Inhibitor: Preclinical Analysis of Efficacy and Selectivity J Pharmacol Exp Ther. December 2008 327:610-619.

Losmapimod is described in e.g. Cheriyan J, Webb A J, Sarov-Blat L, Elkhawad M, Wallace S M, Mäki-Petäjä KM, Collier D J, Morgan J, Fang Z, Willette R N, Lepore J J, Cockcroft J R, Sprecher D L, Wilkinson I B. Inhibition of p38 mitogen-activated protein kinase improves nitric oxide-mediated vasodilatation and reduces inflammation in hypercholesterolemia.

Circulation. 2011 Feb. 8; 123(5):515-23, and is represented by the structural formula indicated below:

Dilmapimod is described in e.g. Christie J D, Vaslef S, Chang P K, May A K, Gunn S R, Yang S, Hardes K, Kahl L, Powley W M, Lipson D A, Bayliffe A I, Lazaar A L. A Randomized Dose-Escalation Study of the Safety and Anti-Inflammatory Activity of the p38 Mitogen-Activated Protein Kinase Inhibitor Dilmapimod in Severe Trauma Subjects at Risk for Acute Respiratory Distress Syndrome. Crit Care Med. 2015 September; 43(9):1859-69, and is represented by the structural formula indicated below:

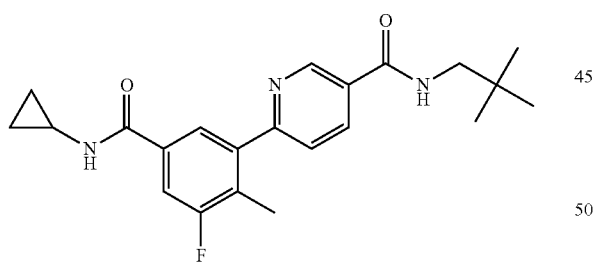

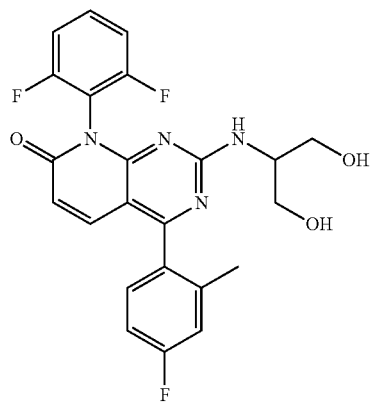 [SMILES: Cc1cc(F)ccc1-c1nc(NC(CO)CO)nc2c1ccc(=O)n2-c1c(F)cccc1F]

LY2228820 is described in e.g. Campbell R M, Anderson B D, Brooks N A, Brooks H B, Chan E M, De Dios A, Gilmour R, Graff J R, Jambrina E, Mader M, McCann D, Na S, Parsons S H, Pratt S E, Shih C, Stancato L F, Starling J J, Tate C, Velasco J A, Wang Y, Ye X S. Characterization of LY2228820 dimesylate, a potent and selective inhibitor of p38 MAPK with antitumor activity. Mol Cancer Ther. 2014 February; 13(2):364-74, and is represented by the structural formula indicated below:

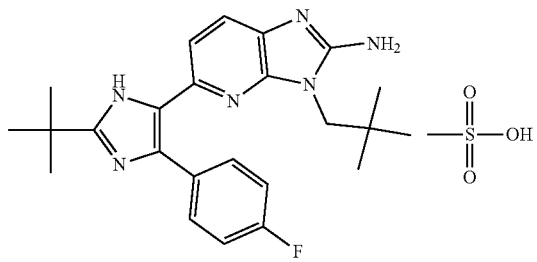

AZD7624 is described in Patel N, Cunoosamy D, Hegelund-Myrback T, Pehrson R, Taib Z, Jansson P, Lundin S, Greenaway S, Clarke G, Siew L. AZD7624, an inhaled p38 inhibitor for COPD, attenuates lung and systemic inflammation after LPS Challenge in humans. Eur Resp J. DOI: 10.1183/13993003.1 September 2015.

ARRY-371797 is described in e.g. Muchir A, Wu W, Choi J C, Iwata S, Morrow J, Homma S, Worman H J. Abnormal p38a mitogen-activated protein kinase signaling in dilated cardiomyopathy caused by lamin A/C gene mutation. Hum Mol Genet. 2012 Oct. 1; 21(19):4325-33 and is represented by the structural formula indicated below:

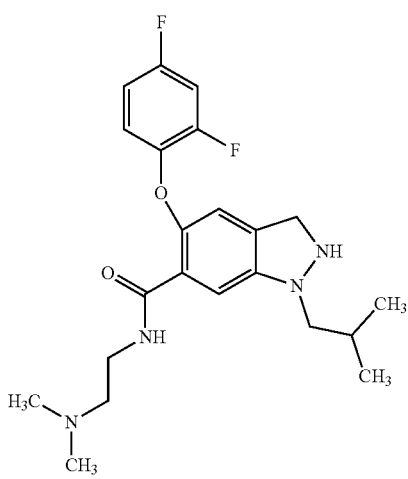 [SMILES: CC(C)CN1NCc2cc(Oc3ccc(F)cc3F)c(C(=O)NCCN(C)C)cc21]

R9111 and its synthesis is described in WO2005/047284 and in e.g. Hill R J, Dabbagh K, Phippard D, Li C, Suttmann R T, Welch M, Papp E, Song K W, Chang K C, Leaffer D, Kim Y-N, Roberts R T, Zabka T S, Aud D, Dal Porto J, Manning A M, Peng S L, Goldstein D M, and Wong B R; Pamapimod, a Novel p38 Mitogen-Activated Protein Kinase Inhibitor: Preclinical Analysis of Efficacy and Selectivity J Pharmacol Exp Ther. December 2008 327:610-619, and is represented by the structural formula indicated below:

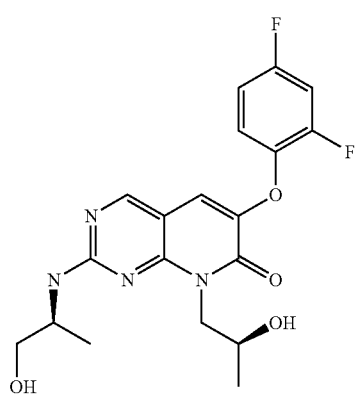 [SMILES: C[C@H](O)Cn1c(=O)c(Oc2ccc(F)cc2F)cc2cnc(N[C@@H](C)CO)nc21]

PH-797804 is described in e.g. Xing L, Devadas B, Devraj R V, Selness S R, Shieh H, Walker J K, Mao M, Messing D, Samas B, Yang J Z, Anderson G D, Webb E G, Monahan J B. Discovery and characterization of atropisomer PH-797804, a p38 MAP kinase inhibitor, as a clinical drug candidate. ChemMedChem. 2012 Feb. 6; 7(2):273-80, and is represented by the structural formula indicated below:

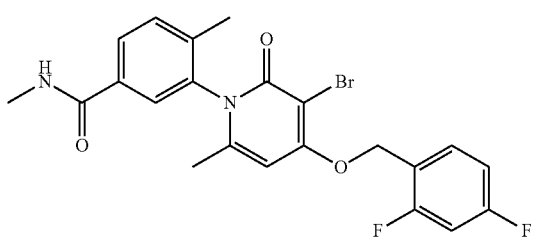 [SMILES: CNC(=O)c1ccc(C)c(-n2c(C)cc(OCc3ccc(F)cc3F)c(Br)c2=O)c1]

BIRB 796 is described in e.g. Dietrich J, Hulme C, Hurley L H. The design, synthesis, and evaluation of 8 hybrid DFG-out allosteric kinase inhibitors: a structural analysis of the binding interactions of Gleevec, Nexavar, and BIRB-796. Bioorg Med Chem. 2010 Aug. 1; 18(15):5738-48, and is represented by the structural formula indicated below:

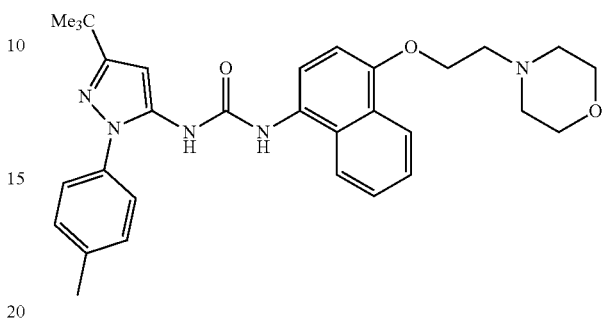

VX-702 is described in e.g. Damjanov N, Kauffman R S, Spencer-Green G T. Efficacy, pharmacodynamics, and safety of VX-702, a novel p38 MAPK inhibitor, in rheumatoid arthritis: results of two randomized, double-blind, placebo-controlled clinical studies. Arthritis Rheum. 2009 May; 60(5): 1232-41, and is represented by the structural formula indicated below:

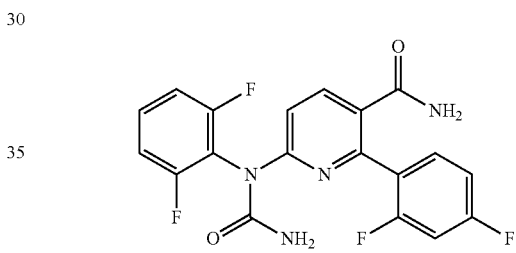

VX-745 is described in e.g. Duffy J P, Harrington E M, Salituro F G, Cochran J E, Green J, Gao H, Bemis G W, Evindar G, Galullo V P, Ford P J, Germann U A, Wilson K P, Bellon S F, Chen G, Taslimi P, Jones P, Huang C, Pazhanisamy S, Wang Y M, Murcko M A, Su M S. The Discovery of VX-745: A Novel and Selective p38t Kinase Inhibitor. ACS Med Chem Lett. 2011 Jul. 28; 2(10):758-63, and is represented by the structural formula indicated below:

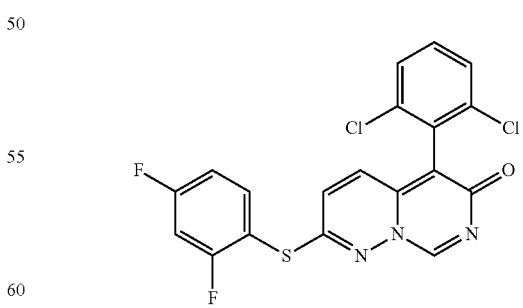

SB239063 is described in e.g. Strassburger M, Braun H, Reymann K G. Anti-inflammatory treatment with the p38 mitogen-activated protein kinase inhibitor SB239063 is neuroprotective, decreases the number of activated microglia and facilitates neurogenesis in oxygen-glucose-deprived hippocampal slice cultures. Eur J Pharmacol. 2008 Sep. 11; 592 (1-3):55-61, and is represented by the structural formula indicated below:

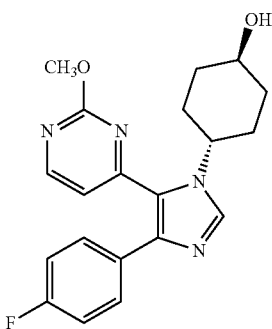

SB202190 is described in e.g. Hirosawa M, Nakahara M, Otosaka R, Imoto A, Okazaki T, Takahashi S. The p38 pathway inhibitor SB202190 activates MEK/MAPK to stimulate the growth of leukemia cells. Leuk Res. 2009 May; 33(5):693-9, and is represented by the structural formula indicated below:

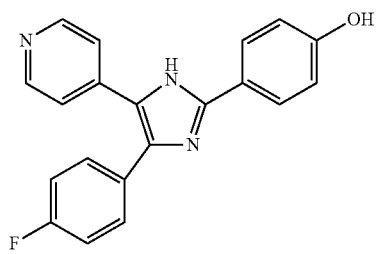 [SMILES: Oc1ccc(-c2nc(-c3ccc(F)cc3)c(-c3ccncc3)[nH]2)cc1]

SCIO469 is described in e.g. Sokol L, Cripe L, Kantarjian H, Sekeres M A, Parmar S, Greenberg P, Goldberg S L, Bhushan V, Shammo J, Hohl R, Verma A, Garcia-Manero G, Li Y P, Lowe A, Zhu J, List A F. Randomized, dose-escalation study of the p38α MAPK inhibitor SCIO-469 in patients with myelodysplastic syndrome. Leukemia. 2013 April; 27(4):977-80, and is represented by the structural formula indicated below:

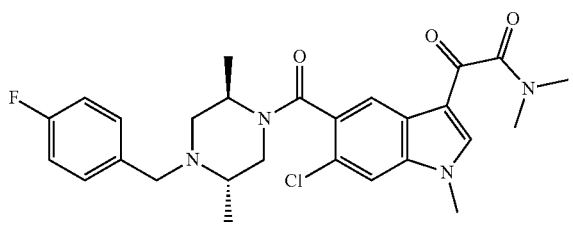 [SMILES: C[C@@H]1CN(Cc2ccc(F)cc2)[C@@H](C)CN1C(=O)c1cc2c(C(=O)C(=O)N(C)C)cn(C)c2cc1Cl]

BMS 582949 is described in e.g. Liu C, Lin J, Wrobleski S T, Lin S, Hynes J, Wu H, Dyckman A J, Li T, Wityak J, Gillooly K M, Pitt S, Shen D R, Zhang R F, McIntyre K W, Salter-Cid L, Shuster D J, Zhang H, Marathe P H, Doweyko A M, Sack J S, Kiefer S E, Kish K F, Newitt J A, McKinnon M, Dodd J H, Barrish J C, Schieven G L, Leftheris K. Discovery of 4-(5-(cyclopropylcarbamoyl)-2-methylphenylamino)-5-methyl-N-propylpyrrolo[1,2-f][1,2,4]triazine-6-carboxamide (BMS-582949), a clinical p38α MAP kinase inhibitor for the treatment of inflammatory diseases. J Med Chem. 2010 Sep. 23; 53(18):6629-39, and is represented by the structural formula indicated below:

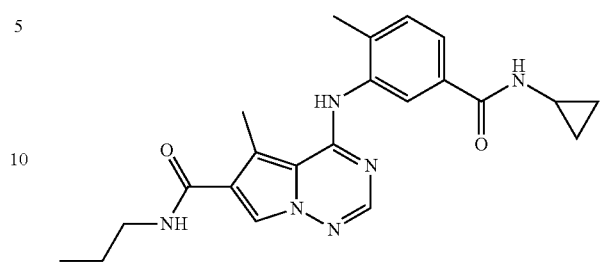

In a further embodiment, there is provided a pharmaceutical composition according to the invention, comprising
(a) a PPAR agonist;
(b) a compound of formula I as defined herein; and optionally
(c) one or more pharmaceutically acceptable diluents, excipients or carriers.

In a further embodiment, there is provided a pharmaceutical composition comprising
(a) a PPAR agonist;
(b) a compound of formula II as defined herein; and optionally
(c) one or more pharmaceutically acceptable diluents, excipients or carriers.

In a further embodiment, there is provided a pharmaceutical composition comprising
(a) a PPAR gamma agonist;
(b) a compound of formula I as defined herein; and optionally
(c) one or more pharmaceutically acceptable diluents, excipients or carriers.

In a further embodiment, there is provided a pharmaceutical composition comprising
(a) a PPAR gamma agonist;
(b) a compound of formula II as defined herein; and optionally
(c) one or more pharmaceutically acceptable diluents, excipients or carriers.

In a preferred embodiment, there is provided a pharmaceutical composition comprising
(a) a PPAR gamma agonist;
(b) a compound of formula I as defined herein; and optionally
(c) one or more pharmaceutically acceptable diluents, excipients or carriers;
wherein said PPAR gamma agonist is selected from the group consisting of pioglitazone, rosiglitazone, troglitazone and INT131 or a pharmaceutically acceptable salt thereof; and
wherein $X^1$ and $X^2$ in said compound of formula I are each O; and
wherein Z in said compound of formula I is N; and
wherein W in said compound of formula I is NH; and
wherein $Ar^1$ in said compound of formula I is aryl; and
wherein $R^1$ in said compound of formula I is heteroalkyl; and
wherein $R^3$ in said compound of formula I is alkyl.

In a further preferred embodiment, there is provided a pharmaceutical composition comprising
(a) a PPAR gamma agonist;
(b) pamapimod or a pharmaceutically acceptable salt thereof or R9111 or a pharmaceutically acceptable salt thereof, preferably pamapimod or a pharmaceutically acceptable salt thereof; and optionally (c) one or more pharmaceutically acceptable diluents, excipients or carriers;

wherein said PPAR gamma agonist is selected from the group consisting of pioglitazone, rosiglitazone and troglitazone or a pharmaceutically acceptable salt thereof.

In a particularly preferred embodiment, there is provided a pharmaceutical composition comprising (a) pioglitazone or a pharmaceutically acceptable salt thereof;

(b) pamapimod or a pharmaceutically acceptable salt thereof; and optionally (c) one or more pharmaceutically acceptable diluents, excipients or carriers.

In a further particularly preferred embodiment, there is provided a pharmaceutical composition comprising (a) pioglitazone hydrochloride;

(b) pamapimod or a pharmaceutically acceptable salt thereof; and optionally (c) one or more pharmaceutically acceptable diluents, excipients or carriers.

Combinations:

As outlined above, the invention relates to a pharmaceutical combination comprising a PPAR agonist, such as pioglitazone or a pharmaceutically acceptable salt thereof and a p38 inhibitor, such as pamapimod or a pharmaceutically acceptable salt thereof. A pharmaceutical combination according to the invention is for example a combined preparation or a pharmaceutical composition, for simultaneous, separate or sequential use.

The term "combined preparation" as used herein defines especially a "kit of parts" in the sense that said PPAR agonist and said p38 inhibitor can be dosed independently, either in separate form or by use of different fixed combinations with distinguished amounts of the active ingredients. The ratio of the amount of PPAR agonist to the amount of p38 inhibitor to be administered in the combined preparation can be varied, e.g. in order to cope with the needs of a patient sub-population to be treated or the needs of a single patient, which needs can be different due to age, sex, body weight, etc. of a patient. The individual parts of the combined preparation (kit of parts) can be administered simultaneously or sequentially, i.e. chronologically staggered, e.g. at different time points and with equal or different time intervals for any part of the kit of parts.

The term "pharmaceutical composition" refers to a fixed-dose combination (FDC) that includes the PPAR agonist and the p38 inhibitor combined in a single dosage form, having a predetermined combination of respective dosages.

The pharmaceutical combination further may be used as add-on therapy. As used herein, "add-on" or "add-on therapy" means an assemblage of reagents for use in therapy, the subject receiving the therapy begins a first treatment regimen of one or more reagents prior to beginning a second treatment regimen of one or more different reagents in addition to the first treatment regimen, so that not all of the reagents used in the therapy are started at the same time. For example, adding p38 inhibitor therapy to a patient already receiving PPAR agonist therapy.

In a preferred embodiment, the pharmaceutical combination according to the invention is a pharmaceutical composition, i.e. a fixed-dose combination.

In a further preferred embodiment, the pharmaceutical combination according to the invention is a combined preparation.

The amount of the PPAR agonist and the p38 inhibitor to be administered will vary depending upon factors such as the particular compound, disease condition and its severity, according to the particular circumstances surrounding the case, including, e.g., the specific PPAR agonist being administered, the route of administration, the condition being treated, the target area being treated, and the subject or host being treated.

In one embodiment, the invention provides a pharmaceutical combination comprising a PPAR agonist and a compound of the formula I or II, wherein said PPAR agonist and said compound of the formula I or II are present in a therapeutically effective amount.

The expression "effective amount" or "therapeutically effective amount" as used herein refers to an amount capable of invoking one or more of the following effects in a subject receiving the combination of the present invention: (i) inhibition or arrest of tumor growth, including, reducing the rate of tumor growth or causing complete growth arrest; (ii) reduction in the number of tumor cells; (iii) reduction in tumor size; (iv) reduction in tumor number; (v) inhibition of metastasis (i.e., reduction, slowing down or complete stopping) of tumor cell infiltration into peripheral organs; (vi) enhancement of antitumor immune response, which may, but does not have to, result in the regression or elimination of the tumor; (vii) relief, to some extent, of one or more symptoms associated with cancer; (viii) increase in progression-free survival (PFS) and/or; overall survival (OS) of the subject receiving the combination.

In another preferred embodiment, the invention provides a pharmaceutical combination comprising a PPAR agonist and a compound of the formula I or II, wherein said PPAR agonist and said compound of the formula I or II are present in an amount producing an additive therapeutic effect.

As used herein, the term "additive" means that the effect achieved with the pharmaceutical combinations of this invention is approximately the sum of the effects that result from using the anti-cancer agents, namely the PPAR agonist and the p38 inhibitor, as a monotherapy. Advantageously, an additive effect provides for greater efficacy at the same doses, and may lead to longer duration of response to the therapy.

In another preferred embodiment, the invention provides a pharmaceutical combination comprising a PPAR agonist and a compound of the formula I or II, wherein said PPAR agonist and said compound of the formula I or II are present in an amount producing a synergistic therapeutic effect.

As used herein, the term "synergistic" means that the effect achieved with the pharmaceutical combinations of this invention is greater than the sum of the effects that result from using the anti-cancer agents, namely the PPAR agonist and the p38 inhibitor, as a monotherapy. Advantageously, such synergy provides for greater efficacy at the same doses, and may lead to longer duration of response to the therapy.

In one embodiment, the invention provides a pharmaceutical combination comprising a p38 inhibitor and a PPAR agonist, wherein the amount of said PPAR agonist in the combination is from about 0.1 to about 50 mg or from about 0.1 to about 45 mg or from about 0.1 to about 30 mg or from about 0.1 to about 15 mg or from about 0.8 to about 10 mg or from about 0.1 to about 5 mg.

In a preferred embodiment, the invention provides a pharmaceutical combination comprising a p38 inhibitor and a PPAR agonist, wherein the amount of said PPAR agonist in the combination is about 1 mg, about 2 mg, about 3 mg, about 4 mg, about 5 mg, about 6 mg, about 7 mg, about 8 mg, about 9 mg or about 10 mg.

In a particularly preferred embodiment, the invention provides a pharmaceutical combination comprising a p38 inhibitor and pioglitazone, wherein the amount of pioglitazone in the combination is about 1 mg, about 2 mg, about 3 mg, about 4 mg, about 5 mg, about 6 mg, about 7 mg, about 8 mg, about 9 mg or about 10 mg.

In one embodiment, the PPAR agonist is administered to the subject at a dose that is below the dose needed for the treatment of diabetes using a PPAR agonist. In a further embodiment, the PPAR agonist is administered to the subject at a dose that is a factor of 8-20 fold lower than the top dose approved for the treatment of diabetes, in particular a factor of 8-20 fold lower than the top dose evaluated and tested for the treatment of diabetes in human. The top dose evaluated and tested for the treatment of diabetes in human e.g for a PPAR gamma agonist such as pioglitazone is usually in the range from about 30-45 mg/day. In yet a further embodiment, at the PPAR dose used, common side effects seen at doses used in the treatment of diabetes are reduced or not detected.

In one embodiment, the PPAR agonist is administered to the subject at a dose that is below the active dose for antidiabetic or anti-dyslipidemic effect of said PPAR agonist, in particular a dose that is below the active dose for antidiabetic or anti-dyslipidemic effect of the PPAR agonist in human.

In a preferred embodiment, the invention provides a pharmaceutical combination comprising a p38 inhibitor and pioglitazone, wherein the amount of pioglitazone in the combination is below the dose typically needed for the treatment of diabetes with pioglitazone. A typical dosing regimen of pioglitazone in the treatment of diabetes is 15 to 45 mg pioglitazone once-daily.

In a particularly preferred embodiment, the invention provides a pharmaceutical combination comprising a p38 inhibitor and pioglitazone, wherein the amount of pioglitazone in the combination is about 5 mg.

In a further particularly preferred embodiment, the invention provides a pharmaceutical combination comprising a p38 inhibitor and pioglitazone, wherein the amount of pioglitazone in the combination is about 2 mg.

In one embodiment, the invention provides a pharmaceutical combination comprising a p38 inhibitor and a PPAR agonist, wherein the amount of said p38 inhibitor in the combination is from about 1 to about 500 mg or from about 1 to about 450 mg or from about 1 to about 400 mg or from about 1 to about 350 mg or from about 1 to about 300 mg or from about 1 to about 250 mg or from about 1 to about 200 mg or from about 1 to about 150 mg or from about 1 to about 125 mg or from about 10 to about 125 mg or from about 10 to about 100 mg or from about 20 to about 100 mg or from about 30 to about 100 mg or from about 40 to about 100 mg or from about 50 to about 100 mg.

In a preferred embodiment, the invention provides a pharmaceutical combination comprising a p38 inhibitor and a PPAR agonist, wherein the amount of said p38 inhibitor in the combination is about 25 mg, about 50 mg, about 75 mg, about 125 mg, about 150 mg or about 300 mg.

In a further preferred embodiment, the invention provides a pharmaceutical combination comprising a p38 inhibitor and a PPAR agonist, wherein the amount of said p38 inhibitor in the combination is about 50 mg, about 75 mg, about 100 mg, or about 150 mg.

In yet a further preferred embodiment, the invention provides a pharmaceutical combination comprising a p38 inhibitor and a PPAR agonist, wherein the amount of said p38 inhibitor in the combination is about 75 mg.

In one embodiment, the invention provides a pharmaceutical combination comprising a p38 inhibitor and a PPAR agonist, wherein the amount of said PPAR agonist in the combination is from about 0.1 to about 50 mg or from about 0.1 to about 45 mg or from about 0.1 to about 30 mg or from about 0.1 to about 15 mg or from about 0.8 to about 10 mg; and wherein the amount of said p38 inhibitor in the combination is from about 1 to about 500 mg or from about 1 to about 450 mg or from about 1 to about 400 mg or from about 1 to about 350 mg or from about 1 to about 300 mg or from about 1 to about 250 mg or from about 1 to about 200 mg or from about 1 to about 150 mg or from about 1 to about 125 mg or from about 10 to about 125 mg or from about 10 to about 100 mg or from about 20 to about 100 mg or from about 30 to about 100 mg or from about 40 to about 100 mg or from about 50 to about 100 mg.

In a preferred embodiment, the invention provides a pharmaceutical combination comprising a p38 inhibitor and a PPAR agonist, wherein the amount of said PPAR agonist in the combination is about 1 mg, about 2 mg, about 3 mg, about 4 mg, about 5 mg, about 6 mg, about 7 mg, about 8 mg, about 9 mg or about 10 mg; and wherein the amount of said p38 inhibitor in the combination is about 50 mg, about 75 mg, about 100 mg, or about 150 mg.

In a particularly preferred embodiment, the invention provides a pharmaceutical combination comprising pamapimod and pioglitazone, wherein the amount of pamapimod in the combination is about 75 mg and wherein the amount of pioglitazone in the combination is from about 2 mg to about 5 mg.

Pharmaceutical Compositions:

As indicated above, the invention also relates to a pharmaceutical composition comprising a PPAR agonist such as pioglitazone and a p38 inhibitor such as pamapimod and at least one pharmaceutically acceptable carrier.

The term "pharmaceutically acceptable carrier" as used herein refers to a carrier or excipient or diluent that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject.

Formulations and Modes of Administration:

A pharmaceutical combination according to the invention is, preferably, suitable for enteral administration, such as oral or rectal administration to a subject and comprises a therapeutically effective amount of the active ingredients and one or more suitable pharmaceutically acceptable carrier.

If not indicated otherwise, a pharmaceutical combination according to the invention is prepared in a manner known per se, e.g. by means of conventional mixing, granulating, coating, dissolving or lyophilizing processes. In preparing a combination for an oral dosage form, any of the usual pharmaceutical media may be employed, for example water, glycols, oils, alcohols, carriers, such as starches, sugars, or microcrystalline cellulose, diluents, granulating agents, lubricants, binders, disintegrating agents and the like. Because of their ease of administration, tablets and capsules represent the most advantageous oral dosage unit forms, in which case solid pharmaceutical carriers are obviously employed.

In one embodiment, the pharmaceutical combination according to the invention is a combination for enteral administration. Preferred are combinations for oral administration. As indicated above, said pharmaceutical combination is preferably a pharmaceutical composition, i.e. fixed-dose combination.

A pharmaceutical combination for enteral administration is, for example, a unit dosage form, such as a tablet, a capsule or a suppository.

In one embodiment, the invention provides a pharmaceutical composition comprising a PPAR agonist, such as pioglitazone and a p38 inhibitor, such as pamapimod and at least one pharmaceutically acceptable carrier, wherein the composition is a tablet or a capsule, preferably a tablet.

In a preferred embodiment, the invention provides a pharmaceutical composition comprising a PPAR agonist, such as pioglitazone and a p38 inhibitor, such as pamapimod and at least one pharmaceutically acceptable carrier, wherein the composition is a sustained release tablet.

In a further preferred embodiment, the pharmaceutical composition according to the invention is for oral administration, wherein the composition is adapted to provide sustained release of the active pharmaceutical ingredients (API). Thus, the composition may increase $T_{max}$ or reduce $C_{max}$, or both increase $T_{max}$ and reduce $C_{max}$, as compared to an immediate release composition.

"$C_{max}$" means the peak concentration of the drug in the plasma. "$T_{max}$" means the time from administration to reach $C_{max}$.

A sustained release composition as compared to an immediate release composition comprises one or more agents which act to prolong release of the API; for example, the API may be embedded in a matrix and/or surrounded by a membrane which, in either case, controls (reduces) the rate of diffusion of the API into the GI tract.

Additional or alternative, e.g. alternative materials which may be included in the composition to provide sustained release are hydrophobic polymers, for example ethyl cellulose or a methacrylic acid polymer, or a combination thereof. Such polymers, whether used singly or in combination, may be comprised in a coating or may be included in admixture with the API (i.e. may be used as a matrix-former), or may be present both in a coating and in admixture with the API.

Further additional or alternative, e.g. alternative materials which may be included in the composition to provide sustained release are insoluble erodible materials, for example a wax or a hydrogenated vegetable oil, or a combination thereof. Such materials, whether used singly or in combination, may be comprised in a coating or may be included in admixture with the API (i.e. may be used as a matrix-former), or may be present both in a coating and in admixture with the API.

The unit content of active ingredients in an individual dose need not in itself constitute a therapeutically effective amount, since such an amount can be reached by the administration of a plurality of dosage units. A composition according to the invention may contain, e.g., from about 10% to about 100% of the therapeutically effective amount of the active ingredients.

Where the pharmaceutical combination according to the invention is a combined preparation, said PPAR agonist need not be administered in the same dosage form as said p38 inhibitor.

Dosing Regimen:

An exemplary treatment regime entails administration once daily, twice daily, three times daily, every second day, twice per week, once per week. The combination of the invention is usually administered on multiple occasions. Intervals between single dosages can be, for example, less than a day, daily, every second day, twice per week, or weekly. The combination of the invention may be given as a continuous uninterrupted treatment. The combination of the invention may also be given in a regime in which the subject receives cycles of treatment interrupted by a drug holiday or period of non-treatment. Thus, the combination of the invention may be administered according to the selected intervals above for a continuous period of one week or a part thereof, for two weeks, for three weeks for four weeks, for five weeks or for six weeks and then stopped for a period of one week, or a part thereof, for two weeks, for three weeks, for four weeks, for five weeks, or for six weeks. The combination of the treatment interval and the non-treatment interval is called a cycle. The cycle may be repeated one or more times. Two or more different cycles may be used in combination for repeating the treatment one or more times. Intervals can also be irregular as indicated by measuring blood levels of said PPAR agonist and/or said p38 inhibitor in the patient. In a preferred embodiment, the pharmaceutical combination according to the invention is administered once daily. In an exemplary treatment regime the PPAR agonist can be administered from 0.1-100 mg per day and the P38 inhibitor can be administered from 1-300 mg per day.

Using the Combinations of the Invention to Treat Cancer

According to a second aspect the present invention provides a pharmaceutical combination as described herein, for use as a medicament.

According to a third aspect the present invention provides a pharmaceutical combination as described herein, for use in a method for the prevention, delay of progression or treatment of cancer in a subject.

Also provided is the use of a pharmaceutical combination as described herein for the manufacture of a medicament for the prevention, delay of progression or treatment of cancer in a subject.

Also provided is the use of a pharmaceutical combination as described herein for the prevention, delay of progression or treatment of cancer in a subject.

Also provided is a method for the prevention, delay of progression or treatment of cancer in a subject, comprising administering to said subject a therapeutically effective amount of a pharmaceutical combination as described herein.

The terms "treatment"/"treating" as used herein includes: (1) delaying the appearance of clinical symptoms of the state, disorder or condition developing in an animal, particularly a mammal and especially a human, that may be afflicted with or predisposed to the state, disorder or condition but does not yet experience or display clinical or subclinical symptoms of the state, disorder or condition; (2) inhibiting the state, disorder or condition (e.g. arresting, reducing or delaying the development of the disease, or a relapse thereof in case of maintenance treatment, of at least one clinical or subclinical symptom thereof); and/or (3) relieving the condition (i.e. causing regression of the state, disorder or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment.

As used herein, "delay of progression" means increasing the time to appearance of a symptom of a cancer or a mark associated with a cancer or slowing the increase in severity of a symptom of a cancer. Further, "delay of progression" as used herein includes reversing or inhibition of disease progression. "Inhibition" of disease progression or disease complication in a subject means preventing or reducing the disease progression and/or disease complication in the subject.

Preventive treatments comprise prophylactic treatments. In preventive applications, the pharmaceutical combination of the invention is administered to a subject suspected of having, or at risk for developing cancer. In therapeutic applications, the pharmaceutical combination is administered to a subject such as a patient already suffering from cancer, in an amount sufficient to cure or at least partially arrest the symptoms of the disease. Amounts effective for this use will depend on the severity and course of the disease, previous therapy, the subject's health status and response to the drugs, and the judgment of the treating physician. In the case wherein the subject's condition does not improve, the pharmaceutical combination of the invention may be administered chronically, which is, for an extended period of time, including throughout the duration of the subject's life in order to ameliorate or otherwise control or limit the symptoms of the subject's disease or condition.

In the case wherein the subject's status does improve, the pharmaceutical combination may be administered continuously; alternatively, the dose of drugs being administered may be temporarily reduced or temporarily suspended for a certain length of time (i.e., a "drug holiday").

Once improvement of the patient's condition has occurred, a maintenance dose of the pharmaceutical combination of the invention is administered if necessary. Subsequently, the dosage or the frequency of administration, or both, is optionally reduced, as a function of the symptoms, to a level at which the improved disease is retained.

In one embodiment of the invention, there is provided a pharmaceutical combination according to the invention, for use in a method for the prevention, delay of progression or treatment of cancer in a subject, wherein the cancer is selected from the group consisting of lung cancer, ovarian cancer, prostate cancer, breast cancer, bladder cancer, liver cancer, cancer of the gastrointestinal (GI) tract, hematological cancer and kidney cancer.

In a preferred embodiment of the invention, there is provided a pharmaceutical combination according to the invention, for use in a method for the prevention, delay of progression or treatment of lung cancer in a subject.

In another preferred embodiment of the invention, there is provided a pharmaceutical combination according to the invention, for use in a method for the prevention, delay of progression or treatment of lung cancer, ovarian cancer or of cancer of the gastrointestinal (GI) tract in a subject.

In a more preferred embodiment of the invention, there is provided a pharmaceutical combination according to the invention, for use in a method for the prevention, delay of progression or treatment of lung cancer, ovarian cancer or of cancer of the gastrointestinal (GI) tract in a subject, wherein said lung cancer is selected from non-small-cell lung carcinoma and small-cell lung carcinoma and is preferably non-small-cell lung carcinoma, wherein said ovarian cancer is preferably epithelial-derived ovarian cancer and wherein said cancer of the GI tract is selected from esophageal cancer, gastric cancer, intestinal cancer, colorectal cancer, and anal cancer, and is preferably colorectal cancer.

In another preferred embodiment of the invention, there is provided a pharmaceutical combination according to the invention, for use in a method for the prevention, delay of progression or treatment of lung cancer or of cancer of the gastrointestinal (GI) tract in a subject.

In a more preferred embodiment of the invention, there is provided a pharmaceutical combination according to the invention, for use in a method for the prevention, delay of progression or treatment of lung cancer or of cancer of the gastrointestinal (GI) tract in a subject, wherein said lung cancer is selected from non-small-cell lung carcinoma and small-cell lung carcinoma and is preferably non-small-cell lung carcinoma and wherein said cancer of the GI tract is selected from esophageal cancer, gastric cancer, intestinal cancer, colorectal cancer, and anal cancer, and is preferably colorectal cancer.

In one embodiment of the invention, there is provided a pharmaceutical combination according to the invention, for use in a method for the prevention, delay of progression or treatment of breast cancer in a subject.

In one embodiment of the invention, there is provided a pharmaceutical combination according to the invention, for use in a method for the prevention, delay of progression or treatment of bladder cancer in a subject.

In one embodiment of the invention, there is provided a pharmaceutical combination according to the invention, for use in a method for the prevention, delay of progression or treatment of liver cancer in a subject.

In one embodiment of the invention, there is provided a pharmaceutical combination according to the invention, for use in a method for the prevention, delay of progression or treatment of cancer of the GI tract in a subject.

In one embodiment of the invention, there is provided a pharmaceutical combination according to the invention, for use in a method for the prevention, delay of progression or treatment of hematological cancer in a subject.

In one embodiment of the invention, there is provided a pharmaceutical combination according to the invention, for use in a method for the prevention, delay of progression or treatment of kidney cancer in a subject.

In a particularly preferred embodiment of the invention, there is provided a pharmaceutical combination according to the invention, for use in a method for the prevention, delay of progression or treatment of lung cancer in a subject, wherein said lung cancer is selected from non-small-cell lung carcinoma and small-cell lung carcinoma. Preferably said lung cancer is non-small-cell lung carcinoma.

In one embodiment of the invention, there is provided a pharmaceutical combination according to the invention, for use in a method for the prevention, delay of progression or treatment of ovarian cancer in a subject, wherein said ovarian cancer is preferably epithelial-derived ovarian cancer.

In one embodiment of the invention, there is provided a pharmaceutical combination according to the invention, for use in a method for the prevention, delay of progression or treatment of prostate cancer in a subject, wherein said prostate cancer is preferably acinar adenocarcinoma.

In one embodiment of the invention, there is provided a pharmaceutical combination according to the invention, for use in a method for the prevention, delay of progression or treatment of breast cancer in a subject, wherein said breast cancer is selected from ductal carcinoma in situ, invasive ductal carcinoma and invasive lobular carcinoma.

In one embodiment of the invention, there is provided a pharmaceutical combination according to the invention, for use in a method for the prevention, delay of progression or treatment of bladder cancer in a subject, wherein said bladder cancer is selected from transitional cell carcinoma, squamous cell carcinoma, small cell carcinoma, adenocarcinoma and sarcoma.

In one embodiment of the invention, there is provided a pharmaceutical combination according to the invention, for use in a method for the prevention, delay of progression or treatment of liver cancer in a subject, wherein said liver cancer is selected from hepatocellular carcinoma, hepatoblastoma and cholangiocarcinoma.

In one embodiment of the invention, there is provided a pharmaceutical combination according to the invention, for use in a method for the prevention, delay of progression or treatment of cancer of the GI tract in a subject, wherein said cancer of the GI tract is selected from esophageal cancer, gastric cancer, intestinal cancer, colorectal cancer, and anal cancer. This embodiment is particularly preferred. Preferably said cancer of the GI tract is colorectal cancer.

In one embodiment of the invention, there is provided a pharmaceutical combination according to the invention, for use in a method for the prevention, delay of progression or treatment of hematological cancer in a subject, wherein said hematological cancer is selected from acute myeloid leukemia (AML), acute lymphoblastic leukemia (ALL), chronic myeloid leukemia (CML), chronic lymphocytic leukemia (CLL), lymphoma, myelodysplastic syndrome (MDS) and multiple myeloma.

In one embodiment of the invention, there is provided a pharmaceutical combination according to the invention, for use in a method for the prevention, delay of progression or treatment of kidney cancer in a subject, wherein said kidney cancer is renal cell adenocarcinoma.

In a preferred embodiment of the invention, there is provided a pharmaceutical combination according to the invention, for use in a method for the prevention, delay of progression or treatment of lung cancer or ovarian cancer in a subject.

In a further preferred embodiment, there is provided a pharmaceutical combination according to the invention, for use in a method for the prevention, delay of progression or treatment of cancer in a subject, wherein the cancer is selected from the group consisting of cancer of the GI tract, hematological cancer and kidney cancer.

In a more preferred embodiment, there is provided a pharmaceutical combination according to the invention, for use in a method for the prevention, delay of progression or treatment of metastatic cancer, preferably metastatic cancer selected from the group consisting of metastatic lung cancer, metastatic ovarian cancer, metastatic prostate cancer, metastatic breast cancer, metastatic bladder cancer, metastatic liver cancer, metastatic cancer of the gastrointestinal (GI) tract, and metastatic kidney cancer, more preferably metastatic cancer of the GI tract, metastatic ovarian cancer or metastatic lung cancer, even more preferably metastatic cancer of the GI tract or metastatic lung cancer, most preferably metastatic cancer of the GI tract selected from metastatic esophageal cancer, metastatic gastric cancer, metastatic intestinal cancer, metastatic colorectal cancer, and metastatic anal cancer, in particular metastatic colorectal cancer, or metastatic lung cancer selected from metastatic non-small-cell lung carcinoma and metastatic small-cell lung carcinoma, in particular metastatic non-small-cell lung carcinoma, in a subject.

In a fourth aspect the present invention provides a pharmaceutical combination comprising:
(a) a PPAR agonist;
(b) a p38 kinase inhibitor; and optionally
(c) one or more pharmaceutically acceptable diluents, excipients or carriers
for use in a method for the prevention, delay of progression or treatment of lung cancer or ovarian cancer in a subject.

Useful PPAR agonists are as defined above. In a preferred embodiment, said PPAR agonist is a PPAR gamma agonist, in particular pioglitazone or a pharmaceutically acceptable salt thereof.

Useful p38 kinase inhibitors are p38 kinase inhibitors inhibiting P38-alpha, P38-beta, P38-gamma or P38-delta or combinations thereof, preferably inhibiting P38-alpha and/or P38-beta, more preferably inhibiting P38-alpha. Further useful p38 kinase inhibitors are compounds of the formula I or II as defined supra. Further useful p38 kinase inhibitors are p38 kinase inhibitors selected from the group consisting of pamapimod, losmapimod, dilmapimod, AZD7624, ARRY-371797, LY2228820, R9111, PH-797804, BIRB 796, VX-702, VX-745 SB 239063, SB202190, SCIO 469, and BMS 582949, or p38 kinase inhibitors selected from the group consisting of pamapimod, losmapimod, dilmapimod, ARRY-371797, LY2228820, R9111, PH-797804, BIRB 796, VX-702, VX-745 SB 239063, SB202190, SCIO 469, and BMS 582949, in particular pamapimod and/or R9111, more particular pamapimod or a pharmaceutically acceptable salt thereof.

Lung cancers or ovarian cancers are as defined as above. Preferred lung cancers are non-small-cell lung carcinoma or small-cell lung carcinoma and more preferably non-small-cell lung carcinoma and preferred ovarian cancer is epithelial-derived ovarian cancer.

In one embodiment, there is provided a pharmaceutical combination comprising:
(a) a PPAR agonist;
(b) a p38 kinase inhibitor; and optionally
(c) one or more pharmaceutically acceptable diluents, excipients or carriers
for use in a method for the prevention, delay of progression or treatment of lung cancer or ovarian cancer in a subject, wherein said p38 kinase inhibitor is preferably inhibiting P38-alpha, P38-beta, P38-gamma or P38-delta or combinations thereof; more preferably inhibiting P38-alpha and/or P38-beta.

In one embodiment, there is provided a pharmaceutical combination comprising:
(a) a PPAR agonist;
(b) a p38 kinase inhibitor; and optionally
(c) one or more pharmaceutically acceptable diluents, excipients or carriers
for use in a method for the prevention, delay of progression or treatment of lung cancer or ovarian cancer in a subject, wherein said p38 kinase inhibitor is selected from the group consisting of pamapimod, losmapimod, dilmapimod, AZD7624, ARRY-371797, LY2228820, R9111, PH-797804, BIRB 796, VX-702, VX-745 SB 239063, SB202190, SCIO 469, and BMS 582949 or a pharmaceutically acceptable salt thereof, or wherein said p38 kinase inhibitor is selected from the group consisting of pamapimod, losmapimod, dilmapimod, ARRY-371797, LY2228820, R9111, PH-797804, BIRB 796, VX-702, VX-745 SB 239063, SB202190, SCIO 469, and BMS 582949 or a pharmaceutically acceptable salt thereof.

In a preferred embodiment, there is provided a pharmaceutical combination comprising:
(a) a PPAR agonist;
(b) pamapimod or a pharmaceutically acceptable salt thereof; and optionally
(c) one or more pharmaceutically acceptable diluents, excipients or carriers
for use in a method for the prevention, delay of progression or treatment of lung cancer or ovarian cancer in a subject.

In a particularly preferred embodiment, there is provided a pharmaceutical combination comprising:
(a) pioglitazone or a pharmaceutically acceptable salt thereof, preferably pioglitazone hydrochloride;
(b) pamapimod or a pharmaceutically acceptable salt thereof; and optionally
(c) one or more pharmaceutically acceptable diluents, excipients or carriers
for use in a method for the prevention, delay of progression or treatment of lung cancer or ovarian cancer in a subject.

In one embodiment, there is provided a pharmaceutical combination comprising:
(a) a PPAR agonist;
(b) a p38 kinase inhibitor; and optionally
(c) one or more pharmaceutically acceptable diluents, excipients or carriers
for use in a method for the prevention, delay of progression or treatment of lung cancer or ovarian cancer in a subject, wherein said PPAR agonist is activating PPAR alpha, PPAR gamma or PPAR delta or combinations thereof.

In one embodiment, there is provided a pharmaceutical combination comprising:
(a) a PPAR agonist;
(b) a p38 kinase inhibitor; and optionally
(c) one or more pharmaceutically acceptable diluents, excipients or carriers
for use in a method for the prevention, delay of progression or treatment of lung cancer or ovarian cancer in a subject, wherein said PPAR agonist is activating PPAR gamma.

In one embodiment, there is provided a pharmaceutical combination comprising:
(a) a PPAR agonist;
(b) a p38 kinase inhibitor; and optionally
(c) one or more pharmaceutically acceptable diluents, excipients or carriers
for use in a method for the prevention, delay of progression or treatment of lung cancer or ovarian cancer in a subject, wherein said PPAR agonist is selected from pioglitazone, troglitazone, rosiglitazone, fenofibrate, clofibrate, gemfibrozil, aleglitazar, muraglitazar, tesaglitazar, ragaglitazar, saroglitazar, GFT505, naveglitazar, GW501516 and INT131 or a pharmaceutically acceptable salt thereof.

In a preferred embodiment, there is provided a pharmaceutical combination comprising:
(a) a PPAR agonist;
(b) a p38 kinase inhibitor; and optionally
(c) one or more pharmaceutically acceptable diluents, excipients or carriers
for use in a method for the prevention, delay of progression or treatment of lung cancer or ovarian cancer in a subject, wherein said PPAR agonist is pioglitazone or a pharmaceutically acceptable salt thereof.

In a further preferred embodiment, there is provided a pharmaceutical combination comprising:
(a) pioglitazone or a pharmaceutically acceptable salt thereof;
(b) a p38 kinase inhibitor; and optionally
(c) one or more pharmaceutically acceptable diluents, excipients or carriers
for use in a method for the prevention, delay of progression or treatment of lung cancer or ovarian cancer in a subject.

In a further preferred embodiment, there is provided a pharmaceutical combination comprising:
(a) pioglitazone hydrochloride;
(b) a p38 kinase inhibitor; and optionally
(c) one or more pharmaceutically acceptable diluents, excipients or carriers
for use in a method for the prevention, delay of progression or treatment of lung cancer or ovarian cancer in a subject.

In a fifth aspect the present invention provides a pharmaceutical combination comprising:
(a) a PPAR agonist;
(b) a p38 kinase inhibitor; and optionally
(c) one or more pharmaceutically acceptable diluents, excipients or carriers
for use in a method for the prevention, delay of progression or treatment of lung cancer or cancer of the GI tract in a subject.

Useful PPAR agonists are as defined above. In a preferred embodiment, said PPAR agonist is a PPAR gamma agonist, in particular pioglitazone or a pharmaceutically acceptable salt thereof.

Useful p38 kinase inhibitors are p38 kinase inhibitors inhibiting P38-alpha, P38-beta, P38-gamma or P38-delta or combinations thereof, preferably inhibiting P38-alpha and/or P38-beta, more preferably inhibiting P38-alpha. Further useful p38 kinase inhibitors are compounds of the formula I or II as defined supra. Further useful p38 kinase inhibitors are p38 kinase inhibitors selected from the group consisting of pamapimod, losmapimod, dilmapimod, AZD7624, ARRY-371797, LY2228820, R9111, PH-797804, BIRB 796, VX-702, VX-745 SB 239063, SB202190, SCIO 469, and BMS 582949, or p38 kinase inhibitors selected from the group consisting of pamapimod, losmapimod, dilmapimod, ARRY-371797, LY2228820, R9111, PH-797804, BIRB 796, VX-702, VX-745 SB 239063, SB202190, SCIO 469, and BMS 582949, in particular pamapimod and/or R9111, more particular pamapimod or a pharmaceutically acceptable salt thereof.

Lung cancers or cancers of the GI tract are as defined as above. Preferred lung cancers are non-small-cell lung carcinoma or small-cell lung carcinoma, and more preferably non-small-cell lung carcinoma and preferred cancers of the GI tract are selected from esophageal cancer, gastric cancer, intestinal cancer, colorectal cancer, and anal cancer, and more preferably colorectal cancer.

In one embodiment, there is provided a pharmaceutical combination comprising:
(a) a PPAR agonist;
(b) a p38 kinase inhibitor; and optionally
(c) one or more pharmaceutically acceptable diluents, excipients or carriers
for use in a method for the prevention, delay of progression or treatment of lung cancer or cancer of the GI tract in a subject, wherein said p38 kinase inhibitor is preferably inhibiting P38-alpha, P38-beta, P38-gamma or P38-delta or combinations thereof; more preferably inhibiting P38-alpha and/or P38-beta.

In one embodiment, there is provided a pharmaceutical combination comprising:
(a) a PPAR agonist;
(b) a p38 kinase inhibitor; and optionally
(c) one or more pharmaceutically acceptable diluents, excipients or carriers
for use in a method for the prevention, delay of progression or treatment of lung cancer or cancer of the GI tract in a subject, wherein said p38 kinase inhibitor is selected from the group consisting of pamapimod, losmapimod, dilmapimod, AZD7624, ARRY-371797, LY2228820, R9111, PH-797804, BIRB 796, VX-702, VX-745 SB 239063, SB202190, SCIO 469, and BMS 582949 or a pharmaceutically acceptable salt thereof, or p38 kinase inhibitor selected from the group consisting of pamapimod, losmapimod, dilmapimod, ARRY-371797, LY2228820, R9111, PH-797804, BIRB 796, VX-702, VX-745 SB 239063, SB202190, SCIO 469, and BMS 582949 or a pharmaceutically acceptable salt thereof.

In a preferred embodiment, there is provided a pharmaceutical combination comprising:
(a) a PPAR agonist;
(b) pamapimod or a pharmaceutically acceptable salt thereof; and optionally
(c) one or more pharmaceutically acceptable diluents, excipients or carriers
for use in a method for the prevention, delay of progression or treatment of lung cancer or cancer of the GI tract in a subject.

In a particularly preferred embodiment, there is provided a pharmaceutical combination comprising:
(a) pioglitazone or a pharmaceutically acceptable salt thereof, preferably pioglitazone hydrochloride;
(b) pamapimod or a pharmaceutically acceptable salt thereof; and optionally
(c) one or more pharmaceutically acceptable diluents, excipients or carriers
for use in a method for the prevention, delay of progression or treatment of lung cancer or cancer of the GI tract in a subject.

In one embodiment, there is provided a pharmaceutical combination comprising:
(a) a PPAR agonist;
(b) a p38 kinase inhibitor; and optionally
(c) one or more pharmaceutically acceptable diluents, excipients or carriers
for use in a method for the prevention, delay of progression or treatment of lung cancer or cancer of the GI tract in a subject, wherein said PPAR agonist is activating PPAR alpha, PPAR gamma or PPAR delta or combinations thereof.

In one embodiment, there is provided a pharmaceutical combination comprising:
(a) a PPAR agonist;
(b) a p38 kinase inhibitor; and optionally
(c) one or more pharmaceutically acceptable diluents, excipients or carriers
for use in a method for the prevention, delay of progression or treatment of lung cancer or cancer of the GI tract in a subject, wherein said PPAR agonist is activating PPAR gamma.

In one embodiment, there is provided a pharmaceutical combination comprising:
(a) a PPAR agonist;
(b) a p38 kinase inhibitor; and optionally
(c) one or more pharmaceutically acceptable diluents, excipients or carriers
for use in a method for the prevention, delay of progression or treatment of lung cancer or cancer of the GI tract in a subject, wherein said PPAR agonist is selected from pioglitazone, troglitazone, rosiglitazone, fenofibrate, clofibrate, gemfibrozil, aleglitazar, muraglitazar, tesaglitazar, ragaglitazar, saroglitazar, GFT505, naveglitazar, GW501516 and INT131 or a pharmaceutically acceptable salt thereof.

In a preferred embodiment, there is provided a pharmaceutical combination comprising:
(a) a PPAR agonist;
(b) a p38 kinase inhibitor; and optionally
(c) one or more pharmaceutically acceptable diluents, excipients or carriers
for use in a method for the prevention, delay of progression or treatment of lung cancer or cancer of the GI tract in a subject, wherein said PPAR agonist is pioglitazone or a pharmaceutically acceptable salt thereof.

In a further preferred embodiment, there is provided a pharmaceutical combination comprising:

(a) pioglitazone or a pharmaceutically acceptable salt thereof;
(b) a p38 kinase inhibitor; and optionally
(c) one or more pharmaceutically acceptable diluents, excipients or carriers
for use in a method for the prevention, delay of progression or treatment of lung cancer or cancer of the GI tract in a subject.

In a further preferred embodiment, there is provided a pharmaceutical combination comprising:
(a) pioglitazone hydrochloride;
(b) a p38 kinase inhibitor; and optionally
(c) one or more pharmaceutically acceptable diluents, excipients or carriers
for use in a method for the prevention, delay of progression or treatment of lung cancer or cancer of the GI tract in a subject.

EXAMPLES

The present examples are intended to illustrate the present invention without restricting it.

Example 1

Evaluation of the Antitumoral Efficacy of Pamapimod and Pioglitazone Hydrochloride Alone and in Combination in a Subcutaneous Xenograft A549 Lung Carcinoma Model in Female Athymic Nude Mice In Vivo General Study Design:

The study consisted of 4 experimental groups, each containing 10 female athymic nude mice after randomization (for details, see Table 1 below). On day 0, $2 \times 10^6$ A549 tumor cells in 100 µl PBS:Matrigel (1:1) were subcutaneously implanted into the left flank of all participating female athymic nude mice. In the following, primary tumor sizes were measured two times weekly (Monday and Friday) by calipering. On day 21, after mean primary tumor volumes had reached approx. 100-200 mm³, 40 tumor-bearing animals were block-randomized into 4 groups of 10 animals each according to the latest primary tumor measurements (block of four after ranking). For block randomization, a robust automated random number generation within individual blocks was used (MS-Excel 2003). On the following day (day 22), treatment was initiated in all groups (see Table 1 for details). Pioglitazone HCL (10 mg/kg) and pamapimod (100 mg/kg) were administered both alone (Groups 2 and 3, respectively) and in combination (Group 4) once daily p.o. on days 22-45. Animals of Group 1 were treated with 10 ml/kg Vehicle Control (0.9% NaCl, 0.5% Methyl Cellulose, 0.4% polysorbate 80, 0.9% benzyl alcohol, pH 4.8) once daily p.o. for the same time period.

The study was terminated on day 46. All animals were sacrificed and necropsy was performed.

Primary tumors were collected and wet weights and volumes determined.

TABLE 1

Study design

| Group | Compound | Dose | Route | Scheme | Number of animals |
|---|---|---|---|---|---|
| 1 | Vehicle Control[1] | 10 ml/kg | p.o. | 1x daily on days 22-45 | 10 |
| 2 | pioglitazone HCl | 10 mg/kg | p.o. | 1x daily on days 22-45 | 10 |

TABLE 1-continued

Study design

| Group | Compound | Dose | Route | Scheme | Number of animals |
|---|---|---|---|---|---|
| 3 | pamapimod | 100 mg/kg | p.o. | 1x daily on days 22-45 | 10 |
| 4 | pioglitazone HCl + pamapimod | 10 mg/kg + 100 mg/kg | p.o. | 1x daily on days 22-45 | 10 |

[1]0.9% NaCl, 0.5% Methyl Cellulose, 0.4% polysorbate 80, 0.9% benzyl alcohol, pH 4.8

Test Animals:

| Strain | female athymic nude (Crl:NU(NCr)-Foxn1$^{nu}$) |
|---|---|
| Source | Charles River GmbH Sandhofer Weg 7; 97633 Sulzfeld; Germany |
| Total number of animals | 54 (40 after randomization) |
| Age at delivery | 4-5 weeks |
| Identification | Labeling by tattoo |
| Acclimatization | 11 days |

Target Cells (Tumor Cells for Implantation):

| Cell Line: | A549 |
|---|---|
| CPQ #: | 011 |
| Origin: | originated from a human Caucasian lung carcinoma |
| Incubation: | at 37° C. with 10% $CO_2$ |
| Storage: | 94% FCS/6% DMSO |

A549 cells were grown in DMEM high Glutamax 1 with 10% FCS, 100 units penicillin/ml, and 100 µg of streptomycin/ml. A549 cells were cultured in a humidified atmosphere of 90% air and 10% carbon dioxide at 37° C. Media were routinely changed every 3 days.

Test Method (Tumor Implantation):

On day 0, $2 \times 10^6$ A549 tumor cells in 100 µl PBS:Matrigel (1:1) were subcutaneously implanted into the left flank of 54 female athymic nude mice. In the following, animal weights were measured three times weekly (Monday, Wednesday and Friday; balance: Mettler Toledo PB602-L). Primary tumor sizes were measured twice weekly by calipering (manual caliper, OMC Fontana). Tumor sizes were calculated according to the formula $W^2 \times L/2$ (L=length and W=the perpendicular width of the tumor, L>W). On day 21, after mean primary tumor volumes had reached approx. 100-200 mm$^3$, 40 tumor-bearing animals were block-randomized into 4 groups of 10 animals each according to the latest primary tumor measurements (block of four after ranking). For block randomization, a robust automated random number generation within individual blocks was used (MS-Excel 2003). On the following day (day 22), treatment was initiated in all groups (see Table 1 for details).

Husbandry:

| Conditions | Optimum hygienic conditions, air-conditioned with 10-15 air changes per hour, and continually monitored environment with target ranges for temperature 22 ± 3° C. and for relative humidity 45-65%, 12 hours artificial fluorescent light/12 hours dark. |
|---|---|
| Accommodation | max. 4 animals per individual ventilated cage (IVC) |
| Diet | M-Zucht ssniff Spezialdiäten GmbH Ferdinand Gabriel Weg 16; D-59494 Soest |
| Water | Community tap water (autoclaved) |

Vehicle Control:

| Identification | Vehicle |
|---|---|
| Description | 0.9% NaCl, 0.5% Methyl Cellulose, 0.4% polysorbate 80, 0.9% benzyl alcohol, pH 4.8 |
| Storage conditions | Formulations were prepared freshly every two weeks and stored protected from light at 2°-8° C. |

Formulation

Recipes for formulations for preclinical studies in mice for pioglitazone HCl and pamapimod are based on a 20 g mouse and 0.2 ml gavage volume. Formulations were prepared freshly every two weeks and stored protected from light at 2°-8° C.

Treatment:

| Method | p.o. |
|---|---|
| Frequency of administration | 1x daily on days 22-45 |
| Dose volume | 10 ml/kg (volumes were adjusted according to individual animal weights) |
| Dose levels | see Table 1 |

Observations:

| Viability/Mortality | Daily |
|---|---|
| Clinical signs | Daily |
| Body weights | Three times weekly (Monday, Wednesday and Friday) |
| Tumor volume | Twice weekly (Monday and Friday) by caliper measurement |

Necropsy:

At necropsy, animals were weighed and killed by cervical dislocation. Primary tumors were collected and wet weights and volumes determined.

Statistical Analysis:

Primary tumor volumes were analyzed using descriptive data analysis (Mean, SEM, Median and interquartile range). Statistical analysis of efficacy data was done using the Mann Whitney test and the unpaired t-test (in parentheses). All data analysis was performed using GraphPad Prism 5 from GraphPad Software, Inc., San Diego, USA.

Results:

The study consisted of four experimental groups, each containing 10 female athymic nude mice after randomization. On day 0, $2 \times 10^6$ A549 tumor cells were subcutaneously implanted into all animals. After randomization, treatment was initiated on day 22. Pioglitazone HCL and pamapimod were both administered alone (Groups 2 and 3, respectively) as well as in combination (Group 4) and evaluated versus their corresponding Vehicle Control (Group 1).

On day 46, the study was terminated, i.e. all animals were sacrificed and a necropsy was performed to assess tumor growth.

Effects of Treatment on Tumor Growth

Figure 2:
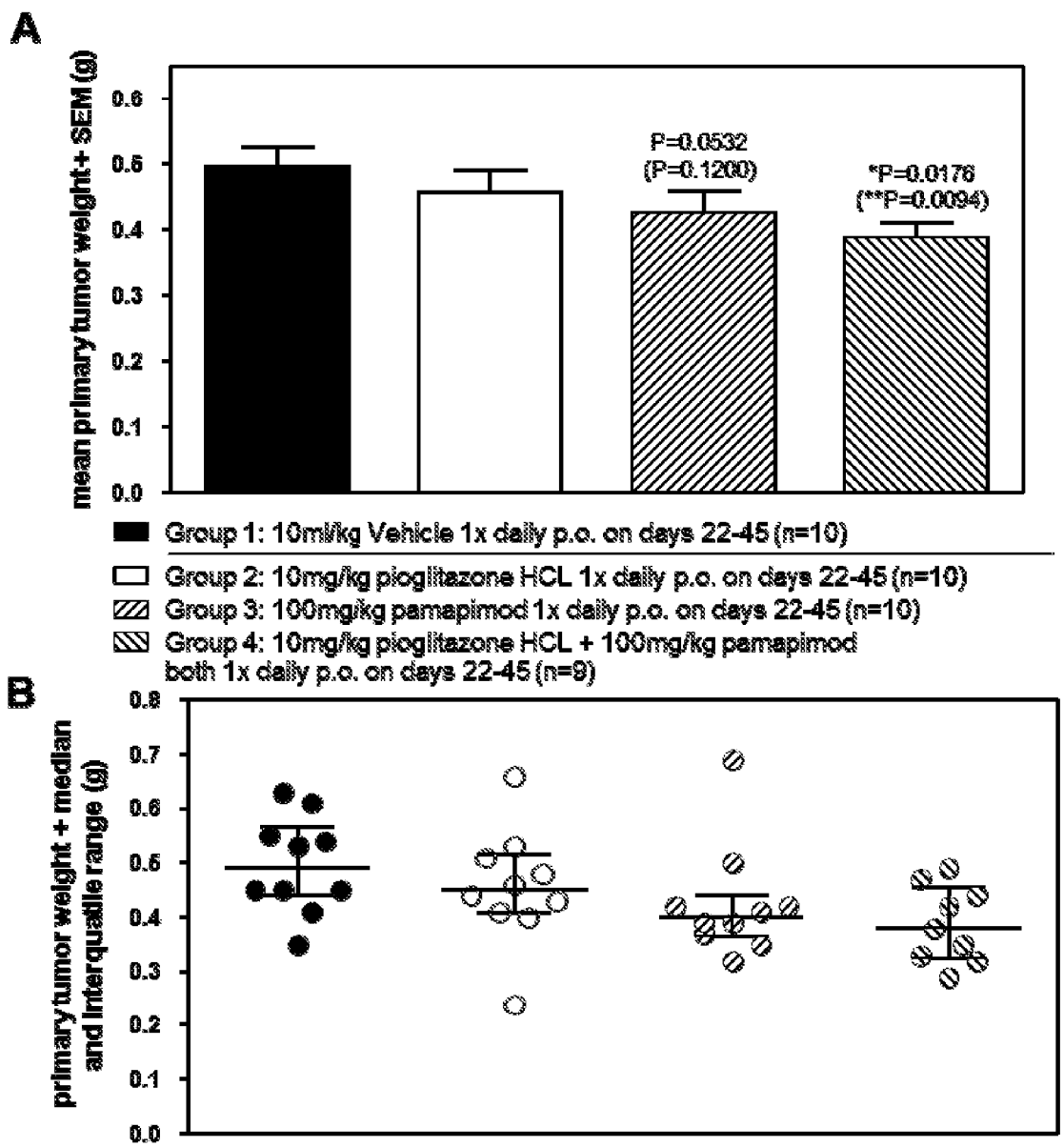
FIG. 2: Primary tumor weights measured at necropsy performed on day 46 of the study in a subcutaneous xenograft A549 lung carcinoma model described in Example 1. Pioglitazone HCL and pamapimod were administered both alone (Groups 2 and 3, respectively) and in combination (Group 4). Data are displayed versus the Vehicle Control (Group 1). Data are depicted both as means+SEM (A) and as individual data points together with their corresponding median values and interquartile ranges (B). P-values were calculated compared to the Vehicle Control (Group 1) by two methods using the Mann Whitney test and the unpaired t-test (in parentheses).

Following necropsy, the primary tumors were excised and tumor volumes and wet weights were determined (FIGS. 1 and 2).

Pioglitazone HCL administered alone (Group 2), caused a noticeable reduction in both tumor volumes and tumor weights compared to control which approached statistical significance.

Pamapimod administered alone (Group 3) also produced a noticeable decrease in both tumor volumes and tumor weights which was significant for tumor volume and nearly significant for tumor weight.

The combination of pioglitazone HCl and pamapimod (Group 4) significantly decreased both tumor volume and tumor weight compared to the vehicle control. Moreover, the magnitude of the effect to decrease tumor volume and weight of the combination of pioglitazone HCl and pamapimod was greater than the effect of either agent alone. These data indicate that the antitumoral efficacy of the two test compounds pioglitazone HCL and pamapimod is clearly greater when administered in combination, compared to single administration.

Example 2

Evaluation of the Antitumoral Efficacy of Pamapimod and Pioglitazone Hydrochloride Alone and in Combination in an Orthotopic Syngeneic CT26 wt Colon Carcinoma Model in Female BALB/c Mice In Vivo General Study Design:

The study consisted of 4 experimental groups, each containing 12 female BALB/c mice after randomization (for details, see Table 1 below). On day 0, $0.5 \times 10^5$ CT26 wt_LLN cells suspended in 15 µl PBS:Matrigel (1:2) were orthotopically implanted into the caecum of all participating animals. In the following period, primary tumor growth was monitored once weekly on days 2, 9, 15 and 20 using in vivo bioluminescence imaging. On day 2, 48 animals were randomized into 4 groups of 12 animals each according to the current in vivo bioluminescence imaging results (block of four after ranking). For block randomization, a robust automated random number generation within individual blocks was used (MS-Excel 2016). Thereby, detected luciferase signals served as randomization criteria. On the following day (day 3), treatment was initiated in all groups (see Table 1 for details). All treatments were performed at 10 ml/kg 1× daily p.o. on days 3-20.

Pioglitazone HCL (25 mg/kg) and pamapimod (100 mg/kg) were administered both alone (Groups 2 and 3, respectively) and in combination (Group 4) once daily p.o. Animals of Group 1 were treated with 10 ml/kg Vehicle Control (0.9% NaCl, 0.5% Methyl Cellulose, 0.4% polysorbate 80, 0.9% benzyl alcohol, pH 4.8) once daily p.o.

On day 20, the study was terminated due to tumor burden All animals were sacrificed and a necropsy performed.

Primary tumors were collected and wet weights and volumes determined.

TABLE 2

Study design

| Group | Compound | Dose | Route | Scheme | Number of animals |
|---|---|---|---|---|---|
| 1 | Vehicle Control[2] | 10 ml/kg | p.o. | 1x daily on days 3-20 | 12 |
| 2 | pioglitazone HCl | 25 mg/kg | p.o. | 1x daily on days 3-20 | 12 |
| 3 | pamapimod | 100 mg/kg | p.o. | 1x daily on days 3-20 | 12 |
| 4 | pioglitazone HCl + pamapimod | 25 mg/kg + 100 mg/kg | p.o. + p.o. | both: 1x daily on days 3-20 | 12 |

1) All animals listed here share the common suffix/16;
2) 0.9% NaCl, 0.5% Methyl Cellulose, 0.4% polysorbate 80, 0.9% benzyl alcohol, pH 4.8

Test Animals:

| | |
|---|---|
| Strain | female BALB/c (BALB/cAnNCrl) |
| Source | Charles River GmbH Sandhofer Weg 7; 97633 Sulzfeld; Germany |
| Total number of animals | 60 (48 after randomization) |
| Age at delivery | 4-5 weeks |
| Identification | Labeling by tattoo |
| Acclimatization | Nov., $18^{th}$ to $22^{nd}$ 2016 |

Target Cells (Tumor Cells for Implantation)

| | |
|---|---|
| Cell Line: | CT26wt_LLN |
| CPQ#: | 364 |
| Origin: | originated from a colon cancer of a BALB/c mouse |
| Parental cell line: | CPQ #238 |
| Incubation: | at 37° C. with 5% $CO_2$ |
| Storage: | 94% FCS/6% DMSO |

The murine CT26 wt tumor cells were previously transfected in order to generate the firefly luciferase expressing cell line CT26 wt_LLN. CT26 wt_LLN cells were grown in RPMI-1640 Glutamax 1, supplemented with 10% FCS, 100 units penicillin/ml and 100 µg of streptomycin/ml. Cells were routinely split every 3 days.

Test Method (Tumor Implantation):

On day 0, prior to surgery, and 24 h after surgery, all animals received the analgetic Meloxicam (Metacam®; 1 mg/kg) via subcutaneous injection. During surgery, the abdominal cave of the mice was incised and the caecum exposed, after mice had been anesthetized with 2.5 volume percent isoflurane in combination with an oxygen flow of 0.6 l/min. $0.5 \times 10^5$ Ct26 wt_LLN cells suspended in 15 µl PBS:Matrigel (1:2) were orthotopically implanted into the caecum of 60 female BALB/c mice. Thereby, cells were carefully injected in between caecum and mesentery. After the caecum had been repositioned, the skin was closed with wound clips. In the following, animal weights were measured three times weekly (Monday, Wednesday and Friday; balance: Mettler Toledo PB602-L). Primary tumor growth was monitored once weekly on days 2, 9, 15 and 20 using in vivo bioluminescence imaging. On day 2, 48 animals were randomized into 4 groups of 12 animals each according to the current in vivo bioluminescence imaging results (block of four after ranking). For block randomization, a robust automated random number generation within individual blocks was used (MS-Excel 2016). Thereby, detected luciferase signals served as randomization criteria. On the following day (day 3), treatment was initiated in all groups (see Table 2 for details).

Husbandry:

| | |
|---|---|
| Conditions | Optimum hygienic conditions, air-conditioned with 10-15 air changes per hour, and continually monitored environment with target ranges for temperature 22 ± 2° C. and for relative humidity 45-65%, 12 hours artificial fluorescent light/12 hours dark. |
| Accommodation | max. 4 animals per individual ventilated cage (IVC) |
| Diet | M-Zucht ssniff Spezialdiäten GmbH Ferdinand Gabriel Weg 16; D-59494 Soest |
| Water | Community tap water (autoclaved) |

Vehicle Control:

| | |
|---|---|
| Identification | Vehicle |
| Description | 0.9% NaCl, 0.5% Methyl Cellulose, 0.4% polysorbate 80, 0.9% benzyl alcohol, pH 4.8 |
| Storage conditions | Formulations were prepared freshly every two weeks and stored protected from light at 2°-8° C. |

Formulations:

Recipes for formulations for preclinical studies in mice for pioglitazone HCl and pamapimod are based on a 20 g mouse and 0.2 ml gavage volume. Formulations were prepared freshly every two weeks and stored protected from light at 2°-8° C.

Treatment:

| | |
|---|---|
| Method | p.o. |
| Frequency of administration | 1x daily on days 3-20 |
| Dose volume | 10 ml/kg (volumes were adjusted according to individual animal weights) |
| Dose levels | see Table 2 |

Observations:

| | |
|---|---|
| Viability/Mortality | Daily |
| Clinical signs | Daily |
| Body weights | Three times weekly (Monday, Wednesday and Friday) |
| Monitoring of tumor growth: | Once weekly on days 2, 9, 15 and 20 using in vivo bioluminescence imaging |

In Vivo Bioluminescence Imaging:

During the course of the study, tumor growth was monitored once weekly on days 2, 9, 15 and 20 using in vivo bioluminescence imaging. For this purpose, 150 mg/kg D-Luciferin were injected intraperitoneally (i.p.) into the mice 7 min before anesthetization. Light emission was measured 10 min post injection with a CCD-camera for 1-5 min using a NightOWL LB 981 bioluminescence imaging system (Berthold Technologies, Germany).

Necropsy:

On day 20, animals were killed by cervical dislocation. Primary tumors were collected, wet weights and volumes determined.

Statistical Analysis:

Primary tumor volumes were analyzed using descriptive data analysis (Mean, SEM, Median and interquartile range). Statistical analysis of efficacy data was done using the Mann Whitney test and the unpaired t-test (in parentheses). All data analysis was performed using GraphPad Prism 5 from GraphPad Software, Inc., San Diego, USA.

Results:

The study consisted of four experimental groups, each containing 12 female BALB/c mice after randomization. On day 0, $0.5 \times 10^5$ CT26 wt_LLN cells suspended in 15 µl PBS:Matrigel (1:2) were orthotopically implanted into the caecum of all participating animals. After animals had been randomized on day 2 according to the in vivo bioluminescence imaging results, treatment was initiated on the following day (day 3). Pioglitazone HCL and pamapimod were both administered alone (Groups 2 and 3, respectively) as well as in combination (Group 4) and evaluated versus their corresponding Vehicle Control (Group 1).

On day 20, the study was terminated, i.e. animals were sacrificed and a necropsy performed to assess tumor growth.

Effects of Treatment on Tumor Growth

General Observations

Figure 3:
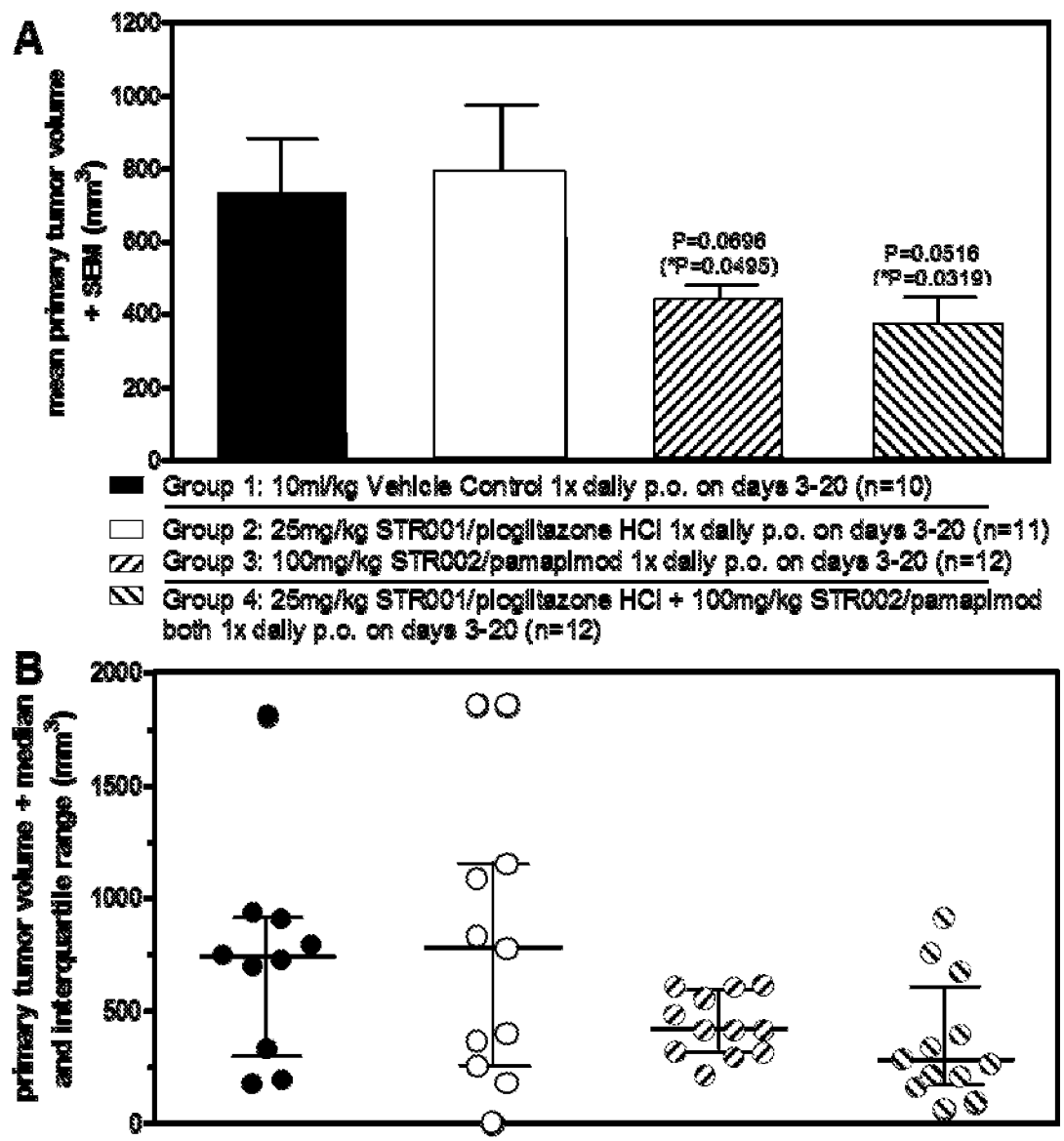
FIG. 3: Primary tumor volumes measures after necropsy on day 20 of the study in an orthotopic syngeneic colon cancer model described in Example 2. Pioglitazone HCL and pamapimod were administered both alone (Groups 2 and 3, respectively) and in combination (Group 4). Data are displayed versus the Vehicle Control (Group 1). Data are depicted both as means+SEM (A) and as individual data points together with their corresponding median values and interquartile ranges (B). P-values were calculated compared to the Vehicle Control (Group 1) by two methods: using the Mann Whitney test and the unpaired t-test (in parentheses).
Figure 4:
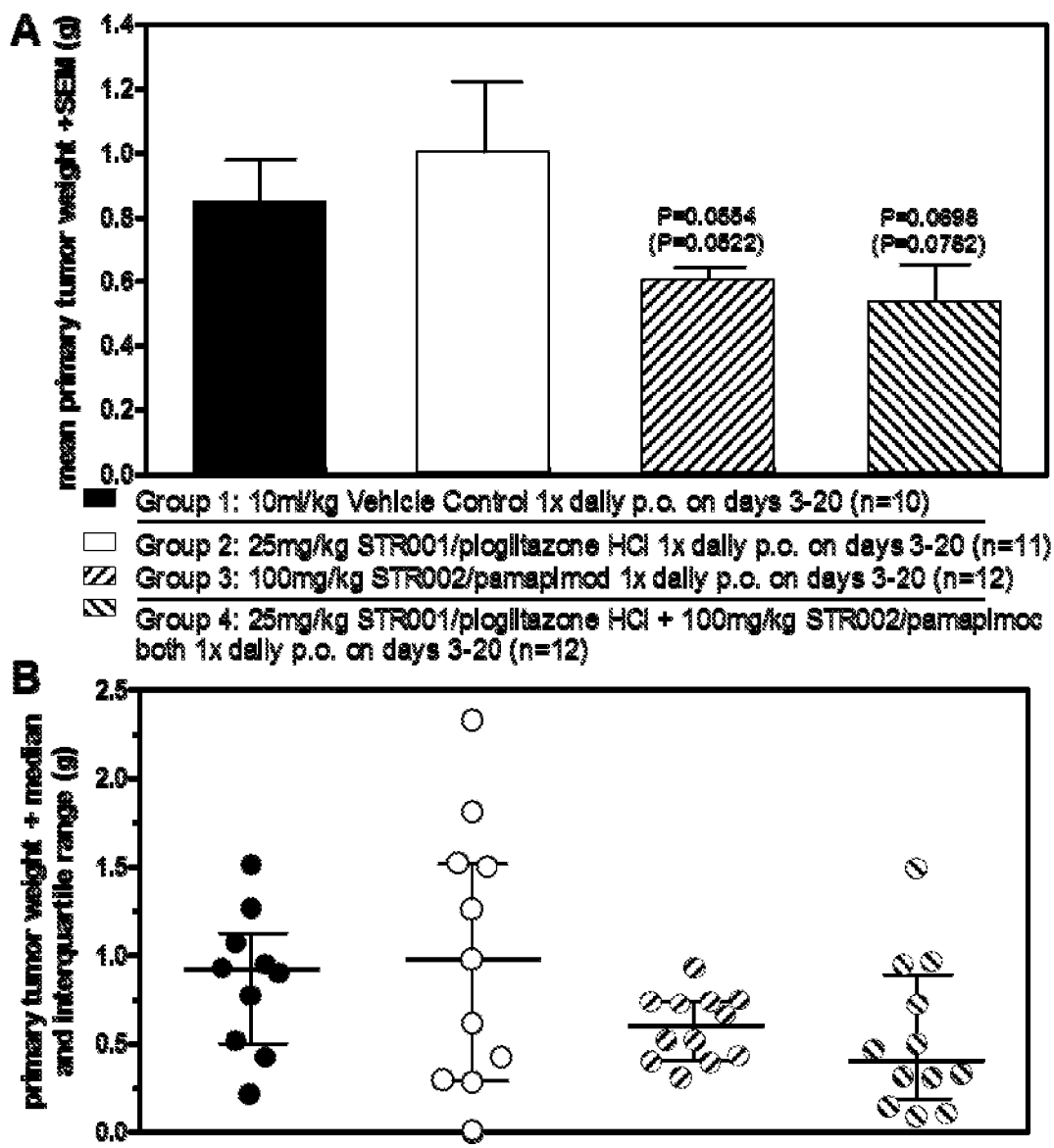
FIG. 4: Primary tumor weight measures after necropsy on day 20 of the study in an orthotopic syngeneic colon cancer model described in Example 2. Pioglitazone HCL and pamapimod were administered both alone (Groups 2 and 3, respectively) and in combination (Group 4). Data are displayed versus the Vehicle Control (Group 1). Data are depicted both as means+SEM (A) and as individual data points together with their corresponding median values and interquartile ranges (B). P-values were calculated compared to the Vehicle Control (Group 1) by two methods using the Mann Whitney test and the unpaired t-test (in parentheses).

Following necropsy, the primary tumors were excised and tumor volumes and wet weights were determined (FIGS. 3 and 4).

Whereas no antitumoral efficacy could be observed for pioglitazone HCL alone (Group 2), pamapimod alone (Group 3) as well as for the combined treatment of both compounds (Group 4), noticeable and comparable antitumoral efficacies could be observed, which were significant in case of primary tumor volumes (FIG. 3) and just beyond significance in case of primary tumor weights (FIG. 4).

Metastases were found in six animals in the control vehicle group, four animals of the pioglitazone group, 2 animals in the pamapimod group and one animal in the piglitazone/pamapimod group. The metastases were located predominantly in the abdominal wall and also in the mesentery.

The combination of pioglitazone HCl and pamapimod (Group 4) showed greater decreases in both tumor volume and tumor weight compared to either agent alone suggesting that pioglitazone potentiates the effect of pamapimod in this particular tumor model. Surprisingly, the number of animals with identifiable metastases was lowest in the combined group compared to either agent alone or the vehicle control, providing for a synergistic effect of the combination. These data indicate that the antitumoral efficacy of the two test compounds pioglitazone HCL and pamapimod is greater when administered in combination, compared to single administration.

The invention claimed is:

1. A pharmaceutical combination comprising:
   (a) a PPAR agonist, wherein said PPAR agonist is pioglitazone or a pharmaceutically acceptable salt thereof;
   (b) 6-(2,4-Difluorophenoxy)-2-[3-hydroxy-1-(2-hydroxyethyl)-propylamino]-8-methyl-8H-pyrido[2,3-d]pyrimidin-7-one (pamapimod, Formula III)

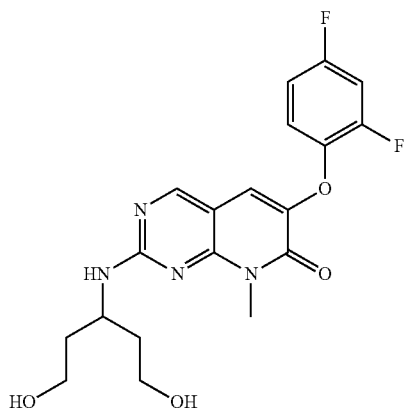

Formula III or a pharmaceutically acceptable salt thereof;

and optionally (c) one or more pharmaceutically acceptable diluents, excipients or carriers.

2. A method for delaying progression of, or treating lung cancer, ovarian cancer, or cancer of the GI tract in a subject, comprising administering the pharmaceutical combination of claim 1 to the subject in need thereof.

3. The method according to claim 2, wherein said pamapimod is a P38 kinase inhibitor which is inhibiting P38-alpha and/or P38-beta.

4. The method according to claim 2, wherein said PPAR agonist is activating PPAR gamma.

\* \* \* \* \*